(12) United States Patent
Cao et al.

(10) Patent No.: US 11,134,881 B2
(45) Date of Patent: Oct. 5, 2021

(54) AUTOMATIC THRESHOLDS FOR ATRIAL TACHYARRHYTHMIA DETECTION IN AN IMPLANTABLE MEDICAL DEVICE

(71) Applicant: Medtronic, Inc., Minneapolis, MN (US)

(72) Inventors: Jian Cao, Shoreview, MN (US); Mark L. Brown, North Oaks, MN (US); Elise J. Higgins, St. Paul, MN (US); Paul J. DeGroot, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 215 days.

(21) Appl. No.: 16/531,390

(22) Filed: Aug. 5, 2019

(65) Prior Publication Data

US 2019/0357795 A1 Nov. 28, 2019

Related U.S. Application Data

(63) Continuation of application No. 15/588,810, filed on May 8, 2017, now Pat. No. 10,368,769.

(Continued)

(51) Int. Cl.
*A61B 5/363* (2021.01)
*A61B 5/00* (2006.01)
(Continued)

(52) U.S. Cl.
CPC .............. *A61B 5/363* (2021.01); *A61B 5/002* (2013.01); *A61B 5/0006* (2013.01);
(Continued)

(58) Field of Classification Search
None
See application file for complete search history.

(56) References Cited

U.S. PATENT DOCUMENTS

| 4,374,382 A | 2/1983 | Markowitz |
| 5,117,824 A | 6/1992 | Keimel et al. |

(Continued)

FOREIGN PATENT DOCUMENTS

WO    199743002 A1    11/1997

OTHER PUBLICATIONS (PCT/US2017/043627) PCT Notification of Transmittal of the International Search Report and the Written Opinion of the International Searching Authority, dated Nov. 10, 2017, 14 pages.

*Primary Examiner* — Kennedy Schaetzle
(74) *Attorney, Agent, or Firm* — Medtronic, Inc.

(57) ABSTRACT

A system for detecting an atrial tachyarrhythmia episode includes a medical device having sensing circuitry configured to receive a cardiac electrical signal from electrodes coupled to the medical device and a processor configured to detect an atrial tachyarrhythmia episode in response to a time duration of the cardiac electrical signal classified as an atrial tachyarrhythmia being greater than or equal to a first detection threshold. The processor is configured to determine if detection threshold adjustment criteria are met based on at least the detected first atrial tachyarrhythmia episode and adjust the first detection threshold to a second detection threshold different than the first detection threshold in response to the detection threshold adjustment criteria being met.

20 Claims, 17 Drawing Sheets

Related U.S. Application Data

(60) Provisional application No. 62/367,177, filed on Jul. 27, 2016.

(51) Int. Cl.

| | | |
|---|---|---|
| *A61B 5/024* | (2006.01) | |
| *G16H 50/30* | (2018.01) | |
| *G16H 40/63* | (2018.01) | |
| *G16H 40/67* | (2018.01) | |
| *A61B 5/316* | (2021.01) | |
| *A61B 5/333* | (2021.01) | |
| *A61B 5/339* | (2021.01) | |
| *A61B 5/352* | (2021.01) | |
| *A61B 5/366* | (2021.01) | |
| *A61N 1/362* | (2006.01) | |
| *A61N 1/365* | (2006.01) | |
| *A61N 1/39* | (2006.01) | |
| *A61B 5/0245* | (2006.01) | |
| *A61B 5/283* | (2021.01) | |

(52) U.S. Cl.
CPC .......... *A61B 5/02405* (2013.01); *A61B 5/316* (2021.01); *A61B 5/333* (2021.01); *A61B 5/339* (2021.01); *A61B 5/352* (2021.01); *A61B 5/366* (2021.01); *A61B 5/4836* (2013.01); *A61B 5/686* (2013.01); *A61B 5/7264* (2013.01); *A61B 5/7275* (2013.01); *A61B 5/746* (2013.01); *A61N 1/3624* (2013.01); *A61N 1/36507* (2013.01); *A61N 1/3925* (2013.01); *A61N 1/3956* (2013.01); *A61N 1/3987* (2013.01); *G16H 40/63* (2018.01); *G16H 40/67* (2018.01); *G16H 50/30* (2018.01); *A61B 5/0245* (2013.01); *A61B 5/283* (2021.01); *A61B 5/6869* (2013.01); *A61B 2505/07* (2013.01)

(56) References Cited

U.S. PATENT DOCUMENTS

| | | |
|---|---|---|
| 5,193,535 A | 3/1993 | Bardy et al. |
| 5,545,186 A | 8/1996 | Olson et al. |
| 6,067,473 A | 5/2000 | Greeninger et al. |
| 6,412,490 B1 | 7/2002 | Lee |
| 6,418,346 B1 | 7/2002 | Nelson et al. |
| 6,442,433 B1 | 8/2002 | Linberg |
| 6,480,745 B2 | 11/2002 | Nelson et al. |
| 6,589,187 B1 | 7/2003 | Dirnberger et al. |
| 6,599,250 B2 | 7/2003 | Webb et al. |
| 7,027,858 B2 | 4/2006 | Cao et al. |
| 7,031,765 B2 | 4/2006 | Ritscher et al. |
| 7,120,491 B1 | 10/2006 | Bailin et al. |
| 7,267,368 B2 | 9/2007 | Lagsdin |
| 7,333,855 B2 | 2/2008 | Gunderson et al. |
| 7,349,737 B2 | 3/2008 | Amblard |
| 7,532,929 B2 | 5/2009 | Mussig et al. |
| 7,537,569 B2 | 5/2009 | Sarkar et al. |
| 7,623,911 B2 | 11/2009 | Sarkar et al. |
| 7,627,368 B2 | 12/2009 | Houben et al. |
| 7,647,107 B2 | 1/2010 | Warman et al. |
| 7,831,304 B2 | 11/2010 | Cao et al. |
| 7,970,468 B1* | 6/2011 | Ostrow .............. A61N 1/37247 607/14 |
| 7,996,084 B2 | 8/2011 | Stylos et al. |
| 8,340,765 B2 | 12/2012 | Boileau et al. |
| 8,639,316 B2 | 1/2014 | Sarkar |
| 8,774,908 B2 | 7/2014 | Stewart |
| 8,923,963 B2 | 12/2014 | Bonner et al. |
| 8,977,350 B2 | 3/2015 | Sarkar et al. |
| 10,617,320 B2* | 4/2020 | Mahajan ............. A61N 1/36514 |
| 2004/0064062 A1* | 4/2004 | Zhou ..................... A61B 5/349 600/515 |
| 2006/0036288 A1 | 2/2006 | Bocek et al. |
| 2008/0051843 A1 | 2/2008 | Li et al. |
| 2010/0317984 A1 | 12/2010 | McCarthy et al. |
| 2011/0130666 A1 | 6/2011 | Dong et al. |
| 2011/0270096 A1 | 11/2011 | Osorio et al. |
| 2012/0101392 A1 | 4/2012 | Bhunia et al. |
| 2015/0088216 A1 | 3/2015 | Gordon et al. |
| 2015/0306375 A1 | 10/2015 | Marshall et al. |
| 2015/0306410 A1 | 10/2015 | Marshall et al. |
| 2016/0113534 A1 | 4/2016 | Cao et al. |
| 2016/0113537 A1 | 4/2016 | Cao et al. |
| 2016/0113577 A1 | 4/2016 | Cao et al. |
| 2016/0158567 A1 | 6/2016 | Marshall et al. |
| 2016/0235315 A1 | 8/2016 | Sarkar et al. |
| 2016/0235320 A1 | 8/2016 | Sarkar et al. |
| 2016/0235321 A1 | 8/2016 | Sarkar et al. |
| 2016/0235992 A1 | 8/2016 | Sarkar et al. |

\* cited by examiner

AUTOMATIC THRESHOLDS FOR ATRIAL TACHYARRHYTHMIA DETECTION IN AN IMPLANTABLE MEDICAL DEVICE

RELATED APPLICATIONS

This application is a Continuation of U.S. patent application Ser. No. 15/588,810, filed May 8, 2017, entitled "AUTOMATIC THRESHOLDS FOR ATRIAL TACHYARRHYTHMIA DETECTION IN AN IMPLANTABLE MEDICAL DEVICE" (published as U.S. Patent Pub. No. 2018/0028086), which claims the benefit of the filing date of U.S. Provisional Patent Application No. 62/367,177, filed Jul. 27, 2016, entitled "AUTOMATIC THRESHOLDS FOR ATRIAL TACHYARRHYTHMIA DETECTION IN AN IMPLANTABLE MEDICAL DEVICE," the content of both of which is incorporated by reference in their entirety.

TECHNICAL FIELD

The disclosure relates generally to cardiac medical devices and, in particular, to an implantable cardiac medical device and method for automatically adjusting a threshold for detecting atrial tachyarrhythmia episodes from sensed cardiac electrical signals.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Atrial tachyarrhythmia includes the disorganized form of atrial fibrillation and varying degrees of organized atrial tachycardia, including atrial flutter. Atrial fibrillation (AF) occurs because of multiple focal triggers in the atrium or because of changes in the substrate of the atrium causing heterogeneities in conduction through different regions of the atria. The ectopic triggers can originate anywhere in the left or right atrium or pulmonary veins. The AV node will be bombarded by frequent and irregular atrial activations but will only conduct a depolarization signal when the AV node is not refractory. The ventricular cycle lengths will be irregular and will depend on the different states of refractoriness of the AV-node.

As more serious consequences of persistent atrial arrhythmias have come to be understood, such as an associated risk of relatively more serious ventricular arrhythmias and stroke, there is a growing interest in monitoring and treating atrial arrhythmias. Implantable cardiac monitors and implantable cardioverter defibrillators (ICDs) may be configured to acquire cardiac electrical signals that can be analyzed for detecting atrial arrhythmias.

SUMMARY

In general, the disclosure is directed to techniques for detecting atrial tachyarrhythmia episodes by an implantable medical device. A medical device operating according to the techniques disclosed herein analyzes a cardiac electrical signal over a plurality of time periods and classifies each of the time periods based on characteristics of the cardiac electrical signal, such as characteristics of the RR-intervals occurring during each of the plurality of time periods. The device may automatically adjust a threshold number of time periods that are classified as atrial tachyarrhythmia which are required in order to detect the atrial tachyarrhythmia.

In one example, the disclosure provides a method for detecting an atrial tachyarrhythmia episode by a medical device, comprising receiving a cardiac electrical signal via electrodes coupled to sensing circuitry of the medical device, detecting an atrial tachyarrhythmia episode by a processor of the medical device in response to a time duration of the cardiac electrical signal classified as an atrial tachyarrhythmia being greater than or equal to a first detection threshold, determining if detection threshold adjustment criteria are met based on at least the detected atrial tachyarrhythmia episode; and adjusting the first detection threshold to a second detection threshold different than the first detection threshold in response to the detection threshold adjustment criteria being met.

In another example, the disclosure provides a medical device for detecting an atrial tachyarrhythmia. The medical device includes sensing circuitry configured to receive a cardiac electrical signal from electrodes coupled to the sensing circuitry, and a processor configured to detect an atrial tachyarrhythmia episode in response to a time duration of the cardiac electrical signal classified as an atrial tachyarrhythmia being greater than or equal to a first detection threshold, determine if detection threshold adjustment criteria are met based on at least the detected atrial tachyarrhythmia episode, and adjust the first detection threshold to a second detection threshold different than the first detection threshold in response to the detection threshold adjustment criteria being met.

In another example, the disclosure provides a non-transitory, computer-readable storage medium storing instructions for causing a processor included in a medical device to perform a method for detecting an atrial tachyarrhythmia episode. The method includes receiving a cardiac electrical signal via electrodes coupled to sensing circuitry of the medical device, detecting an atrial tachyarrhythmia episode in response to a time duration of the cardiac electrical signal classified as an atrial tachyarrhythmia being greater than or equal to a first detection threshold, determining if detection threshold adjustment criteria are met based on at least the detected atrial tachyarrhythmia episode, and adjusting the first detection threshold to a second detection threshold different than the first detection threshold in response to the detection threshold adjustment criteria being met.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In the following description, references are made to illustrative examples for carrying out the methods described herein. It is understood that other variations from these examples may be utilized without departing from the scope of the disclosure. In these various examples, a cardiac electrical signal is used for determining successive ventricular cycle lengths for use in detecting atrial arrhythmias. Ventricular cycle lengths may be determined as intervals between successive R-waves that are sensed from the cardiac electrical signal and attendant to the depolarization of the ventricles. The differences between the successive ventricular cycle lengths, or RR intervals (RRIs), are analyzed for determining evidence of atrial tachyarrhythmia, e.g., atrial fibrillation (AF). As described herein, a time period of the cardiac signal may be classified as AF, non-AF, or unclassified based on an analysis of the RRIs and other factors. When a predetermined number of time periods of the cardiac signal are classified as AF, a medical device operating according to the techniques disclosed herein may detect an AF episode. The device, however, may adjust a classification criterion applied for classifying a time period of the cardiac signal prior to detecting AF and detect AF based on the adjusted classification criterion used for classifying subsequent time periods. Furthermore, the device may automatically adjust the number of time periods required to be classified as AF in order to detect the AF episode.

Aspects of the methods described herein can be incorporated in a variety of implantable or external medical devices having cardiac signal monitoring capabilities, which may or may not include therapy delivery capabilities. Such devices include single chamber, dual chamber or bi-ventricular pacing systems or ICDs that sense the R-waves and deliver an electrical stimulation therapy to the ventricles. The atrial arrhythmia detection methods presently disclosed may also be incorporated in implantable cardiac monitors having implantable electrodes or external cardiac monitors having electrocardiogram (ECG) electrodes coupled to the patient's skin to detect R-waves, e.g., Holter monitors, or within computerized systems that analyze pre-recorded ECG or cardiac electrogram (EGM) data. Embodiments may further be implemented in a patient monitoring system, such as a centralized computer system which processes cardiac electrical signals and other data sent to it by implantable or wearable monitoring devices.

Figure 1:
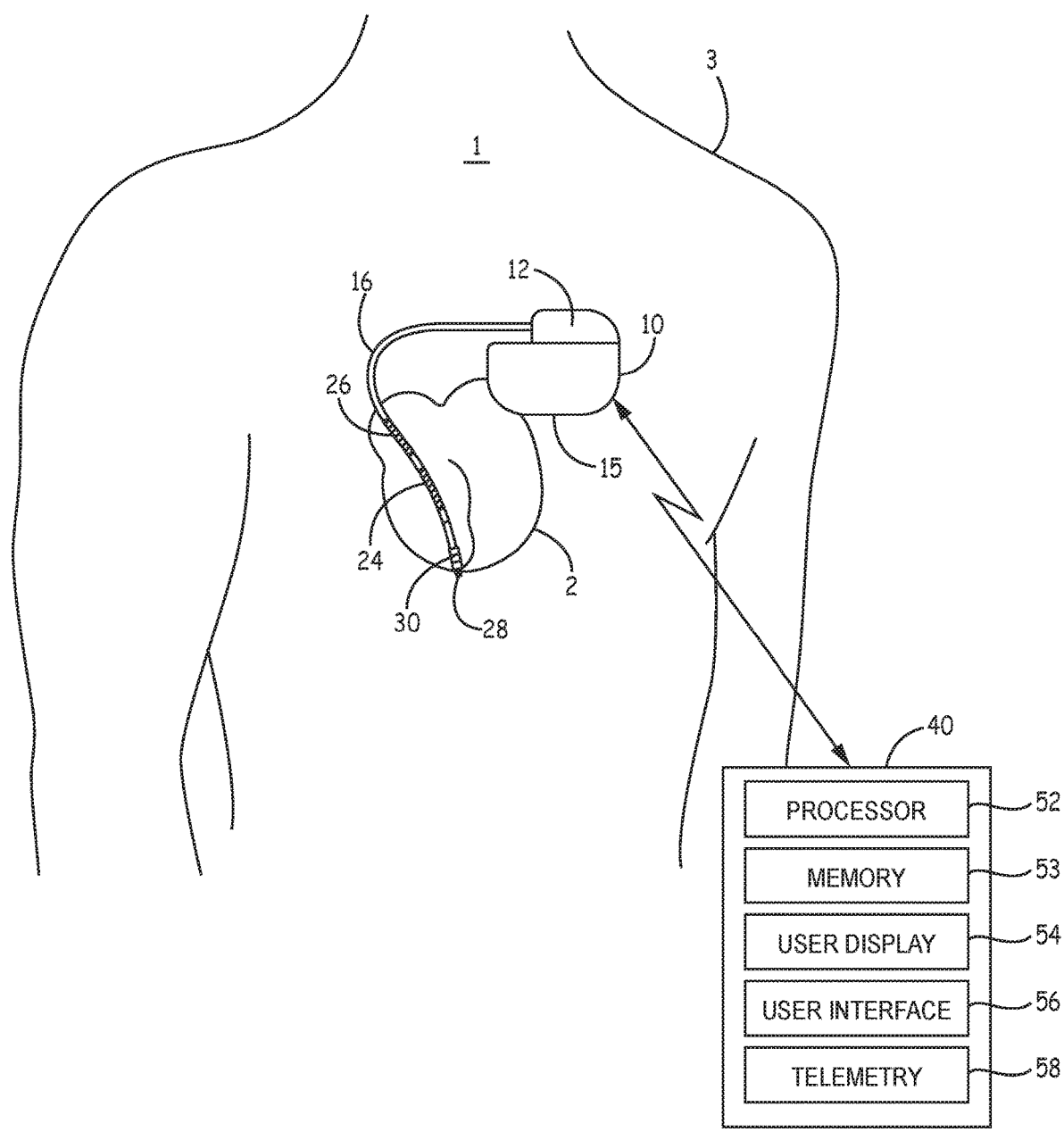
FIG. 1 is a conceptual diagram of an implantable cardioverter defibrillator (ICD) system for detecting atrial arrhythmias according to one example.

FIG. 1 is a conceptual diagram of an implantable medical device (IMD) system 1 for detecting atrial tachyarrhythmias according to one example. The IMD system 1 includes an implantable cardioverter defibrillator (ICD) 10 coupled to a patient's heart 2 via a transvenous electrical medical lead 16. ICD 10 includes a connector block 12 that may be configured to receive the proximal end of lead 16, which is advanced transvenously for positioning electrodes for sensing and stimulation in the right ventricular chamber of heart 2 in the example shown. The techniques disclosed herein may be implemented in a single chamber ICD system 1 that is coupled only to a ventricular lead such as right ventricular (RV) lead 16 for receiving cardiac electrical signals including at least R-waves attendant to the ventricular depolarizations of heart 2.

RV lead 16 is positioned such that its distal end is in the right ventricle for sensing RV cardiac signals and delivering pacing or shocking pulses in the right ventricle. For these purposes, RV lead 16 is equipped with pacing and sensing electrodes shown as a ring electrode 30 and a tip electrode 28. In some examples, tip electrode 28 is an extendable helix electrode mounted retractably within an electrode head. RV lead 16 is further shown to carry defibrillation electrodes 24 and 26, which may be elongated coil electrodes used to deliver high voltage cardioversion/defibrillation (CV/DF) shocks. Defibrillation electrode 24 is referred to herein as the "RV defibrillation electrode" or "RV coil electrode" because it may be carried along RV lead 16 such that it is positioned substantially within the right ventricle when distal pacing and sensing electrodes 28 and 30 are positioned for pacing and sensing in the right ventricle. Defibrillation electrode 26 is referred to herein as a "superior vena cava (SVC) defibrillation electrode" or "SVC coil electrode" because it may be carried along RV lead 16 such that it is positioned at least partially along the SVC when the distal end of RV lead 16 is advanced within the right ventricle.

Each of electrodes 24, 26, 28 and 30 are connected to a respective insulated conductor extending within the body of lead 16. The proximal end of the insulated conductors are coupled to corresponding connectors carried by a proximal lead connector assembly, e.g., an industry standard DF-4 connector, at the proximal end of lead 16, which may be inserted into a connector bore of connector block 12 for providing electrical connection to ICD 10.

The techniques disclosed herein for detecting atrial tachyarrhythmia may be successfully performed without requiring atrial signal sensing. As such, these techniques may be implemented in a single chamber ICD system, such as system 1, which includes a lead extending into the right ventricle for positioning electrodes for sensing ventricular signals but does not include electrodes positioned in or along the atrial chambers for sensing atrial signals. In other examples, other transvenous leads may be present, e.g., a right atrial lead for sensing right atrial signals and delivering electrical stimulation pulses to the right atrium, and/or a left ventricular lead, which may be advanced transvenously into a cardiac vein via the coronary sinus, for sensing left ventricular signals and delivering electrical stimulation pulses to the left atrium. A multi-chamber ICD system in which aspects of the techniques described herein is generally disclosed in U.S. patent application Ser. No. 14/520,798, (Cao et al.), incorporated herein by reference in their entirety.

Electrodes 28 and 30 (and/or coil electrodes 24 and 26) may be used for acquiring cardiac electrical signals needed for performing atrial tachyarrhythmia detection as described herein. R-waves sensed from cardiac electrical signals obtained by ICD 10 are used for determining RRIs between consecutively sensed R-waves for detecting atrial tachyarrhythmia by a processor of ICD 10 based at least in part on an analysis of the RRIs. ICD 10 may be configured to sense cardiac electrical signals from electrodes 24, 26, 28 and/or 30, detect atrial tachyarrhythmia and provide an atrial tachyarrhythmia detection response such as storing atrial tachyarrhythmia episode data for transmission to an external device 40. ICD 10 may additionally be configured to deliver ventricular bradycardia pacing, detect ventricular tachyarrhythmias, and deliver anti-tachycardia pacing therapy and cardioversion/defibrillation shock therapies to the RV via electrodes 24, 26, 28 and/or 30 carried by lead 16.

The RV pacing and sensing electrodes 28 and 30 may be used as a bipolar pair, commonly referred to as a "tip-to-ring" configuration for sensing cardiac electrical signals. In some cases, RV tip electrode 28 may be selected with a coil electrode 24 or 26 to be used as an integrated bipolar pair, commonly referred to as a "tip-to-coil" configuration for sensing cardiac electrical signals. ICD 10 may, for example, select one or more sensing electrode vectors including a tip-to-ring sensing vector between electrodes 28 and 30 and a tip-to-coil or ring-to-coil sensing vector, e.g., between RV tip electrode 28 and SVC coil electrode 26, between RV tip electrode 28 and RV coil electrode 24, between RV ring electrode 30 and SVC coil electrode 26 or between RV ring electrode 30 and RV coil electrode 24. In other examples, any of the electrodes 24, 26, 28 or 30 carried by RV lead 16 may be selected by ICD 10 in a unipolar sensing configuration with the ICD housing 15 serving as the indifferent electrode, commonly referred to as the "can" or "case" electrode. It is recognized that numerous sensing and electrical stimulation electrode vectors may be available using the various electrodes carried by lead 16 and coupled to ICD 10. ICD 10 may be configured to selectively couple one or more sensing electrode vectors to sensing circuitry enclosed by housing 15, e.g., sensing circuitry including one or more amplifiers, filters, rectifiers, comparators, sense amplifiers, analog-to-digital convertors and/or other circuitry configured to acquire a cardiac electrical signal for use in detecting cardiac arrhythmias.

In other examples, the ICD housing 15 may serve as a subcutaneous defibrillation electrode in combination with one or both of the coil electrodes 24 and/or 26 for delivering CV/DF shocks to the atria or ventricles. It is recognized that alternate lead systems may be substituted for the single RV lead system illustrated in FIG. 1. While a particular single-chamber ICD and transvenous lead system 1 is illustrated in FIG. 1, methodologies included in the present disclosure may be adapted for use with any single chamber, dual chamber, or multi-chamber ICD or pacemaker system, subcutaneous implantable device, or other internal or external cardiac monitoring device.

An external device 40 is shown in telemetric communication with ICD 10 by an RF communication link 42. External device 40 is often referred to as a "programmer" because it is typically used by a physician, technician, nurse, clinician or other qualified user for programming operating parameters in ICD 10. External device 40 may be located in a clinic, hospital or other medical facility. External device 40 may alternatively be embodied as a home monitor or a handheld device that may be used in a medical facility, in the patient's home, or another location. Operating parameters, such as sensing and therapy delivery control parameters, may be programmed into ICD 10 using external device 40.

External device 40 includes a processor 52, memory 53, user display 54, user interface 56 and telemetry circuitry 58. Processor 52 controls external device operations and processes data and signals received from ICD 10. According to techniques disclosed herein, processor 52 may receive atrial tachyarrhythmia data obtained by ICD 10 and transmitted from ICD 10 to external telemetry circuitry 58. As described below in conjunction with FIGS. 12 and 16, ICD 10 may be configured to store cardiac signal data associated with detected atrial tachyarrhythmia episodes and transmit the cardiac signal data to external device 40. Processor 52 provides user display 54 with at least a portion of the cardiac electrical signal data for generating a display of the cardiac electrical signal detected as atrial tachyarrhythmia for observation and review by a clinician.

The user display 54 provides a display of the cardiac signal data and may include a graphical user interface that facilitates programming of one or more sensing parameters and/or atrial arrhythmia detection parameters as well as other arrhythmia detection and therapy control parameters by a user interacting with external device 40. External device 40 may display other data and information relating to ICD functions to a user for reviewing ICD operation and programmed parameters as well as cardiac electrical signals or other physiological data that is retrieved from ICD 10 during an interrogation session. User interface 56 may include a mouse, touch screen, or other pointing device, keyboard and/or keypad to enable a user to interact with external device 40 to initiate a telemetry session with ICD 10 for retrieving data from and/or transmitting data to ICD 10 and for selecting and programming desired sensing and therapy delivery control parameters into ICD 10.

Telemetry circuitry 58 includes a transceiver and antenna configured for bidirectional communication with an implantable transceiver and antenna included in ICD 10. Telemetry circuitry 58 is configured to operate in conjunction with processor 52 for encoding and decoding transmitted and received data relating to ICD functions via communication link 42. Communication link 42 may be established between ICD 10 and external device 40 using a radio frequency (RF) link such as BLUETOOTH®, Wi-Fi, Medical Implant Communication Service (MICS) or other RF bandwidth. In some examples, external device 40 may include a programming head that is placed proximate ICD 10 to establish and maintain a communication link, and in other examples external device 40 and ICD 10 may be configured to communicate using a distance telemetry algorithm and circuitry that does not require the use of a programming head and does not require user intervention to maintain a communication link.

It is contemplated that external device 40 may be in wired or wireless connection to a communications network via telemetry circuitry 58 for transferring data to a remote database or computer to allow remote management of the patient 3. Remote patient management systems may be configured to utilize the presently disclosed techniques to enable a clinician to review cardiac electrical signal data and atrial tachyarrhythmia episode data received from ICD 10 and to select and program control parameters transmitted to ICD 10. Reference is made to commonly-assigned U.S. Pat. No. 6,599,250 (Webb et al.), U.S. Pat. No. 6,442,433 (Linberg et al.), U.S. Pat. No. 6,418,346 (Nelson et al.), and U.S. Pat. No. 6,480,745 (Nelson et al.) for general descriptions and examples of remote patient management systems that enable remote patient monitoring and device programming. Each of these patents is incorporated herein by reference in their entirety.

Figure 2A:
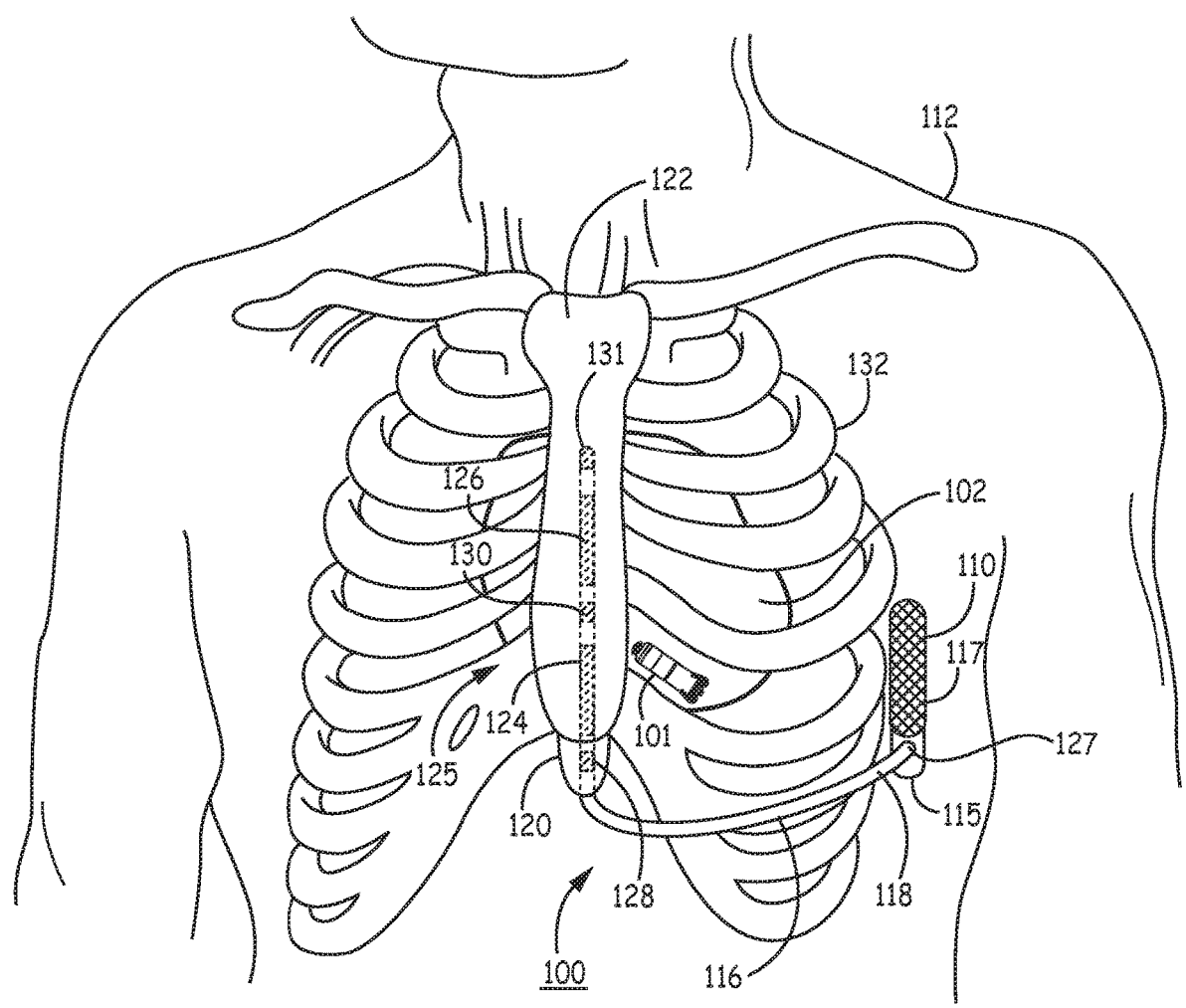
FIGS. 2A and 2B are conceptual diagrams of an alternative ICD system that may be configured to detect atrial tachyarrhythmia according to the techniques disclosed herein.
Figure 2B:
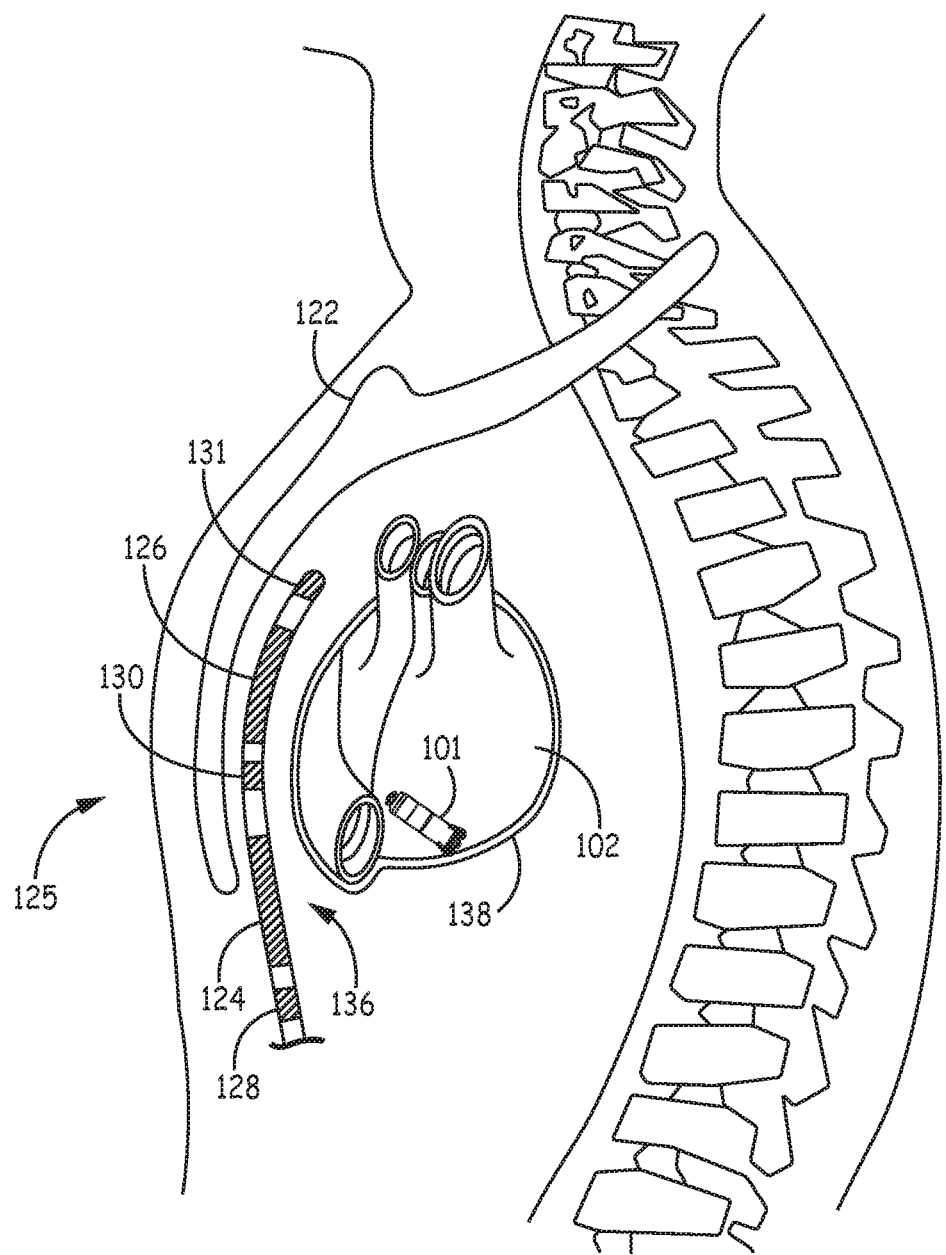

FIGS. 2A and 2B are conceptual diagrams of an alternative ICD system 100 that may be configured to detect atria arrhythmias according to the techniques disclosed herein. FIG. 2A is a front view of an extra-cardiovascular ICD system 100 implanted within patient 112. FIG. 2B is a side view of ICD system 100 implanted within patient 112. ICD system 100 includes an ICD 110 connected to an extra-cardiovascular electrical stimulation and sensing lead 116. ICD system 100 may further include an intracardiac pacemaker 101 configured to deliver pacing pulses to a heart chamber, for example from within the right ventricle or within the left ventricle.

ICD 110 includes a housing 115 that forms a hermetic seal that protects internal components of ICD 110. Internal device components may include circuitry shown and described in conjunction with FIG. 4 below, such as sense amplifier(s), A/D converter, pacing output circuitry, high voltage output circuitry and a microprocessor and memory and/or other control circuitry. The housing 115 of ICD 110 may be formed of a conductive material, such as titanium or titanium alloy. The housing 115 may function as a housing electrode (sometimes referred to as a can electrode). In examples described herein, housing 115 may be used as an active can electrode for use in delivering cardioversion/defibrillation (CV/DF) shocks or other high voltage pulses generated by high voltage charging circuitry of ICD 110. In other examples, housing 115 may be available for use in sensing cardiac signals and/or for delivering unipolar, low voltage cardiac pacing pulses by a pacer output circuit in conjunction with lead-based cathode electrodes. In other instances, the housing 115 of ICD 110 may include multiple electrodes on an outer portion of the housing. The outer portion(s) of the housing 115 functioning as an electrode(s) may be coated with a material, such as titanium nitride.

ICD 110 includes a connector assembly 117 (also referred to as a connector block or header) that includes electrical feedthroughs crossing housing 115 to provide electrical connections between conductors extending within the lead body 118 of lead 116 and electronic components included within the housing 115 of ICD 110. As described below in conjunction with FIG. 4, housing 115 may house one or more processors, memories, telemetry transceivers, sensing circuitry such as sense amplifiers and analog-to digital converters, therapy delivery circuitry such as pacer timing and control, CV/DF control, pace output and HV output circuits and associated charging circuits, a switch matrix, a data bus, one or more batteries or other power sources and other components for sensing cardiac electrical signals, detecting a heart rhythm, and controlling and delivering electrical stimulation pulses to treat an abnormal heart rhythm.

Lead 116 includes an elongated lead body 118 having a proximal end 127 that includes a lead connector (not shown) configured to be connected to ICD connector assembly 117 and a distal portion 125 that includes one or more electrodes. In the example illustrated in FIGS. 2A and 2B, the distal portion 125 of lead 116 includes defibrillation electrodes 124 and 126 and pace/sense electrodes 128, 130 and 131. Electrical conductors (not illustrated) extend through one or more lumens of the elongated lead body 118 of lead 116 from the lead connector at the proximal lead end 127 to electrodes 124, 126, 128, 130 and 131 located along the distal portion 125 of the lead body 118. The lead body 118 of lead 116 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The respective conductors electrically couple the electrodes 124, 126, 128, 130 and 131 to circuitry, such as a switch matrix or other switching circuitry for selection and coupling to a sense amplifier or other cardiac event detection circuitry and/or to a therapy output circuit, e.g., a pacing output circuit or a HV output circuit for delivering CV/DF shock pulses. Connections between electrode conductors and ICD circuitry is made via connections in the connector assembly 117, including associated electrical feedthroughs crossing housing 115. The electrical conductors transmit therapy from an output circuit within ICD 110 to one or more of defibrillation electrodes 124 and 126 and/or pace/sense electrodes 128, 130 and 131 and transmit sensed electrical signals from one or more of defibrillation electrodes 124 and 126 and/or pace/sense electrodes 128, 130 and 131 to the sensing circuitry within ICD 110.

ICD 110 may obtain electrical signals corresponding to electrical activity of heart 102 via a combination of sensing vectors that include combinations of electrodes 128, 130, and/or 131. In some examples, housing 115 of ICD 110 is used in combination with one or more of electrodes 128, 130 and/or 131 in a sensing electrode vector. ICD 110 may even obtain cardiac electrical signals using a sensing vector that includes one or both defibrillation electrodes 124 and/or 126, e.g., between electrodes 124 and 126 or one of electrodes 124 or 126 in combination with one or more of electrodes 128, 130, 131, and/or the housing 115.

ICD 110 analyzes the cardiac electrical signals received from one or more of the sensing vectors to monitor for abnormal rhythms, such as AF, VT and VF. ICD 110 generates and delivers electrical stimulation therapy in response to detecting a ventricular tachyarrhythmia (e.g., VT or VF). ICD 110 may deliver ATP in response to VT detection, and in some cases may deliver ATP prior to a CV/DF shock or during high voltage capacitor charging in an attempt to avert the need for delivering a CV/DF shock. ICD 110 may deliver a CV/DF shock pulse when VF is detected or when VT is not terminated by ATP.

Electrodes 124 and 126 (and in some examples housing 115) are referred to herein as defibrillation electrodes because they are utilized, individually or collectively, for delivering high voltage stimulation therapy (e.g., cardioversion or defibrillation shocks). Electrodes 124 and 126 may be elongated coil electrodes and generally have a relatively high surface area for delivering high voltage electrical stimulation pulses compared to low voltage pacing and sensing electrodes 28, 30 and 31. However, electrodes 124 and 126 and housing 115 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 124 and 126 for use in only high voltage cardioversion/defibrillation shock therapy applications. Electrodes 124 and 126 may be used in a pacing electrode vector for delivering extra-cardiovascular pacing pulses such as ATP pulses, post-shock pacing or other pacing therapies and/or in a sensing vector used to sense cardiac electrical signals for detecting atrial and ventricular arrhythmias, including AF, atrial flutter, VT and VF.

Electrodes 128, 130 and 131 are relatively smaller surface area electrodes for delivering low voltage pacing pulses and for sensing cardiac electrical signals. Electrodes 128, 130 and 131 are referred to as pace/sense electrodes because they are generally configured for use in low voltage applications, e.g., used as either a cathode or anode for delivery of pacing pulses and/or sensing of cardiac electrical signals.

The pace/sense electrodes 128, 130 and/or 131 may be located at different locations along the length of lead 116 than shown. In other examples, lead 116 may include less than three pace/sense electrodes or more than three pace/sense electrodes and/or a single defibrillation electrode or more than two electrically isolated or electrically coupled defibrillation electrodes or electrode segments. Various example configurations of extra-cardiovascular leads and electrodes and dimensions that may be implemented in conjunction with the AF detection techniques disclosed herein are described in commonly-assigned U.S. patent application Ser. No. 14/519,436, U.S. patent application Ser. No. 14/695,255 and provisionally-filed U.S. Pat. Application No. 62/089,417, all of which are incorporated herein by reference in their entirety.

Lead 16 extends subcutaneously or submuscularly over the ribcage 132 medially from the connector assembly 127 of ICD 110 toward a center of the torso of patient 112, e.g., toward xiphoid process 120 of patient 112. At a location near xiphoid process 120, lead 116 bends or turns and extends superiorly within anterior mediastinum 136 in a substernal position. Lead 116 of system 100 is implanted at least partially underneath sternum 122 of patient 112.

Anterior mediastinum 136 may be viewed as being bounded laterally by pleurae, posteriorly by pericardium 138, and anteriorly by sternum 122. In some instances, the anterior wall of anterior mediastinum 136 may also be formed by the transversus thoracis muscle and one or more costal cartilages. Anterior mediastinum 136 includes a quantity of loose connective tissue (such as areolar tissue), adipose tissue, some lymph vessels, lymph glands, substernal musculature, small side branches of the internal thoracic artery or vein, and the thymus gland. In one example, the distal portion 125 of lead 116 extends along the posterior side of sternum 122 substantially within the loose connective tissue and/or substernal musculature of anterior mediastinum 136.

A lead implanted such that the distal portion 125 is substantially within anterior mediastinum 136 may be referred to as a "substernal lead." In the example illustrated in FIGS. 2A and 2B, lead 116 extends substantially centered under sternum 122. In other instances, however, lead 116 may be implanted such that it extends in a position that is offset laterally from the center of sternum 122. In some instances, lead 116 may extend laterally such that distal portion 125 of lead 116 is underneath/below the ribcage 132 in addition to or instead of sternum 122. In other examples, the distal portion 125 of lead 116 may be implanted in other extra-cardiovascular, intra-thoracic locations, including the pleural cavity or around the perimeter of and adjacent to but typically not within the pericardium 138 of heart 102.

In other examples, lead 116 may remain outside the thoracic cavity and extend subcutaneously or submuscularly over the ribcage 132 and/or sternum 122. The path of lead 116 may depend on the location of ICD 110, the arrangement and position of electrodes carried by the lead distal portion 125, and/or other factors.

ICD 110 is shown implanted subcutaneously on the left side of patient 112 along the ribcage 132. ICD 110 may, in some instances, be implanted between the left posterior axillary line and the left anterior axillary line of patient 112. ICD 110 may, however, be implanted at other subcutaneous or submuscular locations in patient 112. For example, ICD 110 may be implanted in a subcutaneous pocket in the pectoral region. In this case, lead 116 may extend subcutaneously or submuscularly from ICD 110 toward the manubrium of sternum 122 and bend or turn and extend inferior from the manubrium to the desired location subcutaneously or submuscularly. In yet another example, ICD 110 may be placed abdominally.

In some patients, an intracardiac pacemaker 101 may be present in the right ventricle, right atrium or along the left ventricle. Pacemaker 101 may be configured to deliver pacing pulses in the absence of sensed intrinsic heart beats, in response to detecting VT, or according to other pacing therapy algorithms. For example, pacemaker 101 may be implanted in the right ventricle of the patient for providing single chamber ventricular pacing. The techniques disclosed herein for classifying time periods of a cardiac signal for detecting atrial tachyarrhythmia may be utilized in the presence of ventricular pacing delivered by ICD 110 and/or by an intracardiac pacemaker such as pacemaker 101. Pacemaker 101 may generally correspond to the intra-cardiac pacemaker disclosed in U.S. Pat. No. 8,923,963 (Bonner, et al.), incorporated herein by reference in its entirety. ICD 110 may be configured to detect pacing pulses delivered by pacemaker 101. The frequency of pacing pulses delivered by pacemaker 101 may be a factor determined in classifying a cardiac electrical signal time period for AF detection purposes.

Pacemaker 101 may have limited processing power and therapy delivery capacity compared to ICD 110 such that the advanced cardiac rhythm detection techniques disclosed herein may be implemented in ICD 110 rather than in pacemaker 101. The methods disclosed herein as being performed by ICD 10 or ICD 110, however, are not to be considered limited to being implemented in an ICD. Aspects of the atrial tachyarrhythmia detection techniques disclosed herein may be implemented in pacemaker 101, all or in part.

Figure 3:
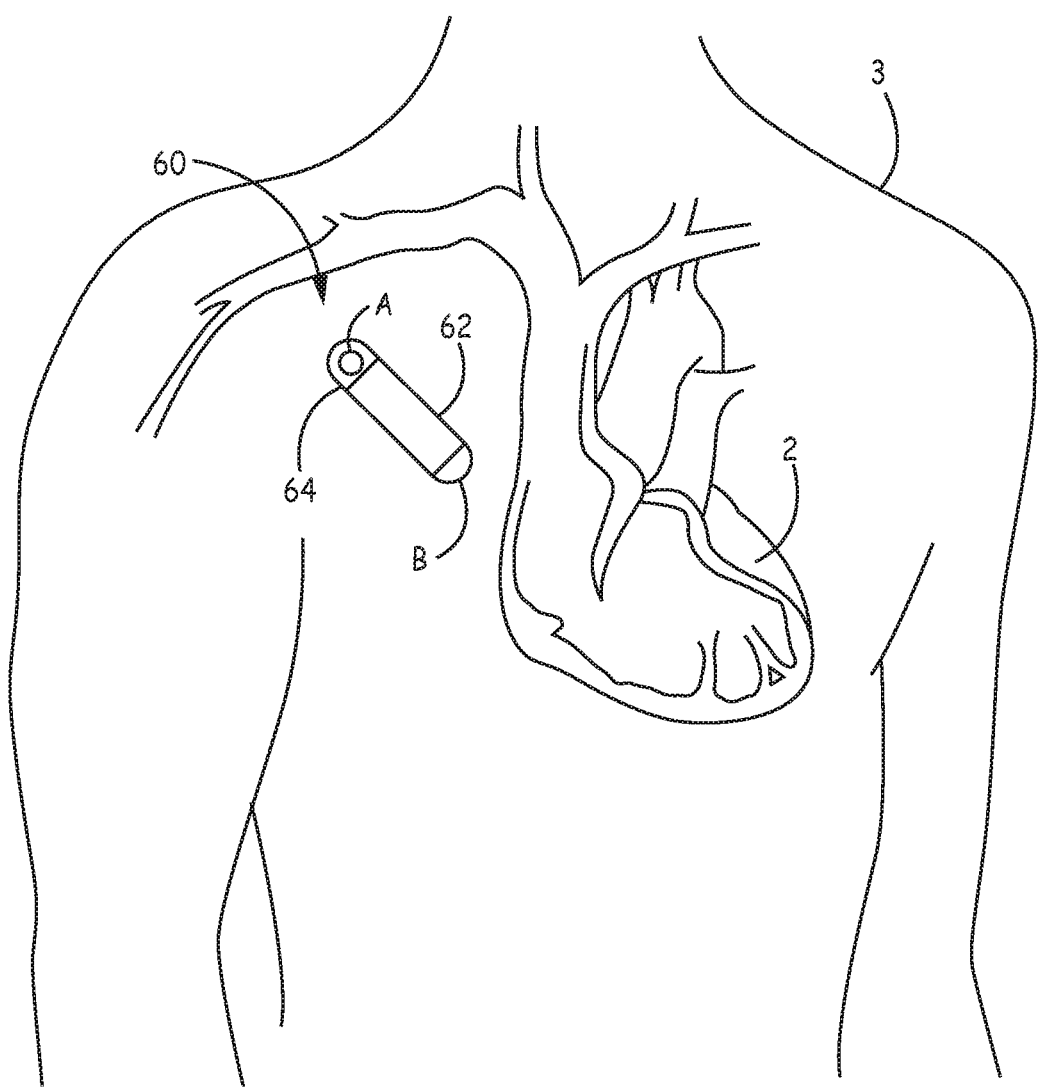
FIG. 3 is a conceptual diagram of an implantable medical device (IMD) system for detecting atrial tachyarrhythmia according to another example.

FIG. 3 is a conceptual diagram of a cardiac monitoring device 60 which may employ aspects of the atrial tachyarrhythmia detection techniques disclosed herein. Monitoring device 60 is shown implanted subcutaneously in the upper thoracic region of a patient's body 3 and displaced from the patient's heart 2. The housing 62 of cardiac monitor 60 (shown enlarged in scale compared to the patient's body 3) includes a non-conductive header module 64 attached to a hermetically sealed housing 62. The housing 62 contains the circuitry of the cardiac monitor 60 and is generally electrically conductive but may be covered in part by an electrically insulating coating. A first, subcutaneous, sense electrode, A, is formed on the surface of the header module 64. In some examples, one or more electrodes may be incorporated in the header module 64. A second, subcutaneous, sense electrode, B, is formed by at least a portion of the housing 62. For example, electrode B may be an exposed portion of housing 62 when housing 62 is coated by an electrically insulating coating. The conductive housing electrode B may be directly connected with the sensing circuitry.

An electrical feedthrough extends through the mating surfaces of the header module 64 and the housing 62 to electrically connect the first sense electrode A with sensing circuitry enclosed within the housing 62. The electrical signals attendant to the depolarization and re-polarization of the heart 2 are referred to as the cardiac electrical signals and are sensed across the sense electrodes A and B and include at least R-waves attendant to the ventricular depolarizations of heart 2. The cardiac monitoring device 60 may be sutured to subcutaneous tissue at a desired orientation of its electrodes A and B to the axis of the heart 2 to detect and record the cardiac electrical signals in a sensing vector A-B for subsequent processing and uplink telemetry transmission to an external device 40 (shown in FIG. 1).

In one embodiment, the spacing between electrodes A and B may range from 60 mm to 25 mm. In other embodiments, the electrode spacing may range from 55 mm to 30 mm, or from 55 mm to 35 mm. The volume of the implantable cardiac monitoring device 60 may be three cubic centimeters or less, 1.5 cubic centimeters or less or any volume between three and 1.5 cubic centimeters. The length of cardiac monitoring device 60 may range from 30 to 70 mm, 40 to 60 mm or 45 to 60 mm and may be any length between 30 and 70 mm. The width of a major surface such a cardiac monitoring device 60 may range from 3 to 10 mm and may be any thickness between 3 and 10 mm. The thickness of cardiac monitoring device 60 may range from 2 to 9 mm or 2 to 5 mm and may be any thickness between 2 and 9 mm.

The sensing circuitry included in housing 62 is configured to detect R-waves for monitoring for atrial tachyarrhythmia according to the techniques disclosed herein. Such sensing circuitry may include a pre-filter and amplifier, an analog-to-digital filter, a rectifier, a sense amplifier, a comparator and/or other components configured to receive cardiac electrical signals and detect R-waves from the signals. Aspects of a cardiac monitoring device of the type that may employ atrial tachyarrhythmia detection techniques disclosed herein are generally disclosed in U.S. Publication No. 2015/0088216 (Gordon, et al.) and U.S. Pat. No. 7,027,858 (Cao, et al.), both incorporated herein by reference in its entirety.

In general, the hermetically sealed housing 62 includes a lithium battery or other power source, a processor and memory or other control circuitry that controls device operations and records arrhythmic cardiac electrical signal episode data in memory registers or bins, and a telemetry transceiver and antenna circuit that receives downlink telemetry commands from and transmits stored data in a telemetry uplink to an external device 40 (FIG. 1). The circuitry and memory may be implemented in discrete logic or a microcomputer based system with A/D conversion of sampled cardiac electrical signal amplitude values. One implantable cardiac monitor that can be modified in accordance with the presently disclosed techniques is described in U.S. Pat. No. 6,412,490 (Lee et al.), incorporated herein by reference in its entirety, as well as the cardiac monitors disclosed in any of the above-incorporated references.

Figure 4:
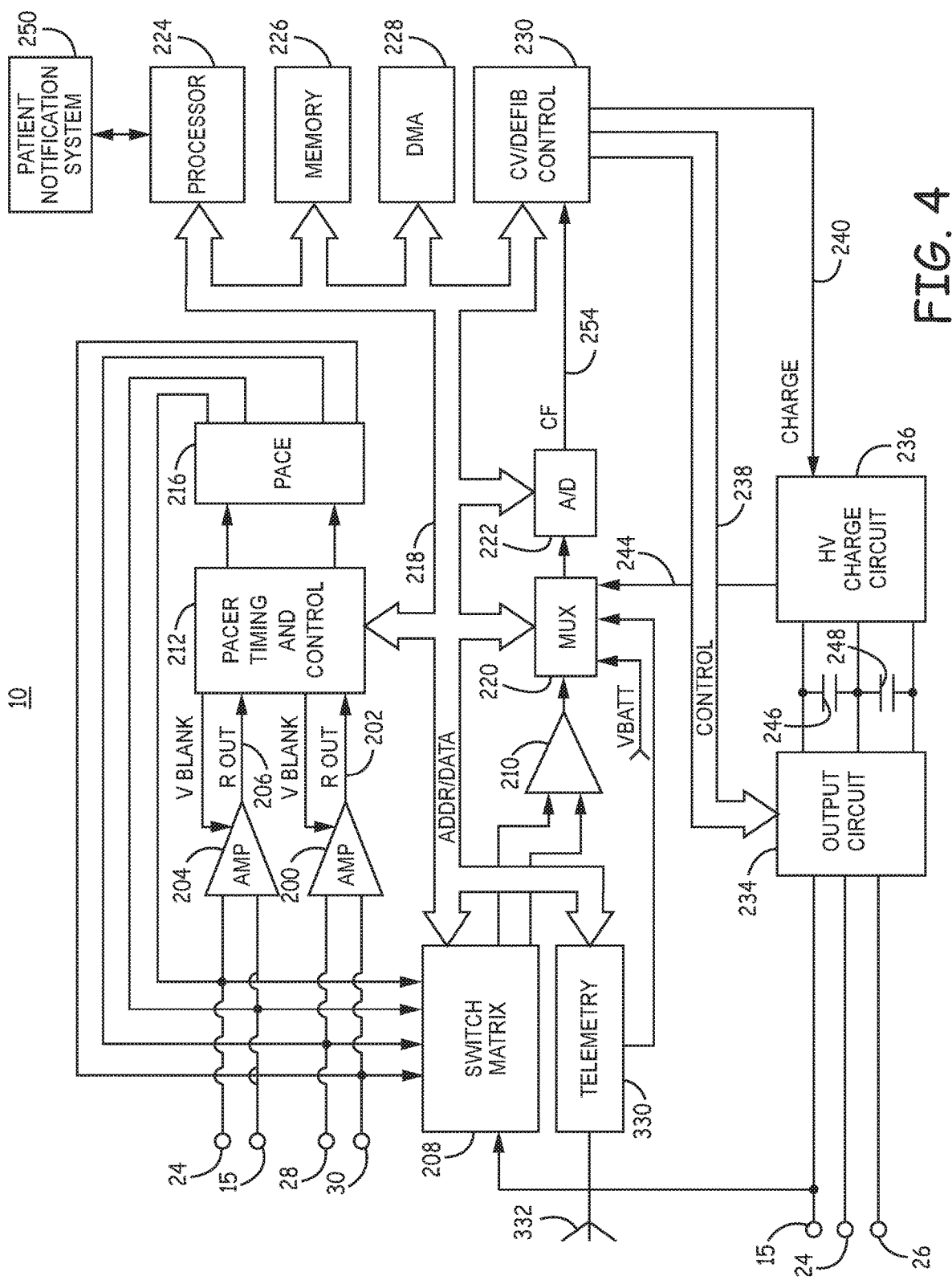
FIG. 4 is a functional schematic diagram of an ICD, such as the ICD of FIG. 1 or the ICD of FIGS. 2A and 2B.

FIG. 4 is a functional schematic diagram of an ICD, such as ICD 10 of FIG. 1 or ICD 110 of FIGS. 2A and 2B. This diagram should be taken as illustrative of the type of device with which the techniques disclosed herein may be embodied and not as limiting. The example shown in FIG. 4 is a microprocessor-controlled device, but the disclosed methods may also be practiced with other types of devices such as those employing dedicated digital circuitry.

With regard to the electrode system illustrated in FIG. 1, ICD 10 is provided with a number of connection terminals for achieving electrical connection to the RV lead 6 and its respective electrodes. Housing 15 may be used as an indifferent electrode during unipolar stimulation or sensing or as an active can electrode during shock delivery. Electrodes 24, 26 and housing 15 may be selectively coupled to the high voltage output circuit 234 to facilitate the delivery of high energy shocking pulses to the heart using one or more of the coil electrodes 24 and 26 and optionally the housing 15.

RV tip electrode 28 and the RV ring electrode 30 may be coupled to a ventricular sense amplifier 200 for sensing ventricular signals. The ventricular sense amplifier 200 may take the form of automatic gain controlled amplifiers with adjustable sensitivity. ICD 10 and, more specifically, microprocessor 224 may automatically adjust the sensitivity of ventricular sense amplifier 200 in response to detection of oversensing in order to reduce the likelihood of oversensing of cardiac events and/or non-cardiac noise.

Ventricular sense amplifier 200 may receive timing information from pacer timing and control circuitry 212. For example, ventricular sense amplifier 200 may receive blanking period input, e.g., V_BLANK, which indicates the amount of time the amplifier is "turned off" in order to prevent saturation due to an applied pacing pulse or defibrillation shock. The general operation of the ventricular sense amplifier 200 may correspond to that disclosed in U.S. Pat. No. 5,117,824 (Keimel, et al.), incorporated herein by reference in its entirety.

Whenever a signal received by ventricular sense amplifier 200 exceeds a ventricular sensitivity, a signal is generated on the R-out signal line 202. As described below, a signal on the R-out signal line 202, which may be referred to as a ventricular sense event (Vs event) signal, may be received by microprocessor 224 and used for determining RRI differences.

Switch matrix 208 is used to select which of the available electrodes 24, 26, 28 and 30 (or 124, 126, 128 and 130 of FIG. 2A) are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. For example, while RV electrodes 28 and 30 are shown coupled to sense amplifier 200 and pace output circuit 216 suggesting dedicated pace/sense electrodes and coil electrodes 24 and 26 are shown coupled to HV output circuit 234 suggesting dedicated CV/DV shock electrodes, it is recognized that switching circuitry included in switch matrix 208 may be used to select any of the available electrodes in a sensing electrode vector, a pacing electrode vector, or a CV/DF shock vector as described previously.

Signals from the electrodes selected for coupling to bandpass amplifier 210 are provided to multiplexer 220, and thereafter converted to multi-bit digital signals by A/D converter 222, for storage in random access memory 226 under control of direct memory access circuit 228 via data/address bus 218. Microprocessor 224 may employ digital signal analysis techniques to characterize the digitized signals stored in random access memory 226 to recognize and classify the patient's heart rhythm employing any of numerous signal processing methodologies for analyzing cardiac signals and cardiac event waveforms, e.g., R-waves. One tachyarrhythmia detection system is described in U.S. Pat. No. 5,545,186 (Olson et al.), incorporated herein by reference in its entirety.

ICD 10 or ICD 110 may include a second sensing channel including sense amplifier 204 receiving a V BLANK signal from pace timing and control 212 and providing an R OUT signal line 206. In the example shown, a sensing electrode vector including electrodes 28 and 30 is coupled to amplifier 200 and a second sensing electrode vector including electrode 24 and housing 15 is coupled to the second amplifier 204. Switch matrix 208 may select which sensing electrode vector selected from any of electrodes 24, 26, 28 and 30 and housing 15 (or electrodes 124, 126, 128 130 and 131 and housing 115 in the case of ICD 110) is coupled to each of the two sensing channels represented by sense amplifiers 200 and 204 and which pacing electrode vector is coupled to pace output circuit 216.

It is to be understood that the circuitry shown in FIG. 4 may be modified according to the particular device requirements. For example, the single chamber ICD 10 of FIG. 1 or extravascular ICD 110 of FIG. 2A may include one ventricular sense amplifier 200 and terminals for electrically coupling to electrodes 24, 26, 28 and 30 and/or housing 15 (or electrodes 124, 126, 128, 130 or 131 and/or housing 115 in any desired sensing electrode vector combination.

Upon detection of an arrhythmia, an episode of cardiac signal data, along with sensed intervals and corresponding annotations of sensed events, may be stored in random access memory 226. The cardiac electrical signals received via sensing electrode pairs may be stored in RAM 226. In some cases, a near-field and a far-field signal are received by the two amplifiers 200 and 204. Typically, a near-field sensing electrode pair includes a tip electrode and a ring electrode located in the ventricle, electrodes 28 and 30. A far-field sensing electrode pair includes electrodes spaced further apart such as any of: the defibrillation coil electrodes 24 or 26 with housing 15; a tip electrode 28 with housing 15; a tip electrode 28 with a defibrillation coil electrode 24 or 26. The use of near-field and far-field signal detecting arrhythmia episodes is described in U.S. Pat. No. 5,193,535 (Bardy), incorporated herein by reference in its entirety. Annotation of sensed events, which may be displayed and stored with cardiac signal data, is described in U.S. Pat. No. 4,374,382 (Markowitz), incorporated herein by reference in its entirety.

The techniques disclosed herein may be applied to one or more cardiac electrical signals acquired using any combination of the available electrodes. In some examples, the sensing circuitry of ICD 10 (or ICD 110) includes more than two sensing channels for acquiring more than two cardiac electrical signals. For example, a first cardiac electrical signal is acquired between the ICD housing 15 and RV coil electrode 24, a second cardiac electrical signal is acquired between the RV coil electrode 24 and the SVC coil electrode 26, and a third cardiac electrical signal is acquired between the RV tip electrode 28 and the RV ring electrode 30. All three signals may be collected and used by microprocessor 224 for analyzing R-waves and RRIs and detecting atrial and/or ventricular arrhythmias. As discussed below in conjunction with FIG. 12, at least two cardiac signals may be stored in RAM 226 when a tachyarrhythmia episode is detected for transmission by telemetry circuit 330 to external device 40. When atrial tachyarrhythmia is detected, with or without simultaneous detection of ventricular tachyarrhythmia, the two signals may be stored having two different gain settings to provide two different signals for display on external device 40. One signal displayed at a higher gain may result in R-wave clipping but enables relatively small amplitude P-waves to be more readily observed, which enables any relationship between the detected atrial and ventricular tachyarrhythmia (if present) to be observed by a clinician through comparison of the two different signals. When ventricular tachyarrhythmia is detected without atrial tachyarrhythmia detection, two signals may be stored both having a gain setting that avoids clipping of R-waves.

The telemetry circuit 330 includes a transceiver for receiving downlink telemetry from and sending uplink telemetry to external device 40 using antenna 332. Telemetry circuit 330 provides bi-directional telemetric communication with an external device 40 as described above.

ICD 10 may receive programmable operating parameters and algorithms via telemetry circuit 330 for storage in RAM 226 and accessed by microprocessor 224 for controlling ICD functions. For example, cardiac rhythm detection parameters and therapy control parameters used by ICD 10 may be programmed via telemetry circuit 330.

Data stored or acquired by ICD 10, including physiological signals or associated data derived therefrom, results of device diagnostics, and histories of detected arrhythmia episodes and delivered therapies, may be retrieved from ICD 10 by the external device 40 following an interrogation command received by telemetry circuit 330. Data to be uplinked to the external device and control signals for the telemetry circuit 330 are provided by microprocessor 224 via address/data bus 218. Received telemetry is provided to microprocessor 224 via multiplexer 220. Numerous types of telemetry systems known for use in implantable medical devices may be implemented in ICD 10.

Other circuitry shown in FIG. 2 is illustrative of therapy delivery circuitry that may be included in an ICD or other implantable medical device employing the atrial arrhythmia detection technique disclosed herein when the device is configured for providing cardiac pacing, cardioversion and defibrillation therapies. For example, the pacer timing and control circuitry 212 may include programmable digital counters which control the basic time intervals associated with various single, dual or multi-chamber pacing modes or anti-tachycardia pacing therapies delivered in the atria or ventricles. Pacer timing and control circuity 212 also sets the amplitude, pulse width, polarity or other characteristics of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pace output circuit 214 and ventricular pace output circuit 216. The pace output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias. Microprocessor 224 may also track the number of pacing pulses delivered, particularly the number of ventricular pacing pulses delivered, during predetermined time periods as a factor used in classifying the cardiac electrical signal during the time period.

The microprocessor 224 includes associated read-only memory (ROM) in which stored programs controlling the operation of the microprocessor 224 reside. A portion of the random access memory (RAM) 226 may be configured as a number of recirculating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microprocessor 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In some examples, the ICD 10 may be equipped with a patient notification system 250. Any patient notification method known for use in implantable medical devices may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 (Greeninger et al.), incorporated herein by reference in its entirety. In some examples, ICD 10 provides a response to an atrial tachyarrhythmia detection by generating a patient notification via system 250 and/or a clinician notification using telemetry circuit 330. An atrial tachyarrhythmia response provided by ICD 10 may include determining an AF burden as the total combined duration of all detected AF episodes during a predetermined monitoring time interval, e.g., 24 hours, and generating a patient notification and/or clinician notification when the AF burden exceeds a threshold.

In the following description, AF detection techniques are described with reference to the circuitry of FIG. 4 of ICD 10 of FIG. 1 or ICD 110 of FIGS. 2A and 2B. It is to be understood, however, that the methods and techniques of the descriptions that follow may be implemented in a cardiac monitoring device such as the device of FIG. 3 or even an intracardiac pacemaker such as the intracardiac pacemaker 110 of FIGS. 2A and 2B, all of which devices may include a microprocessor, memory and sensing circuitry, as generally described in conjunction with FIG. 4, for performing these atrial tachyarrhythmia detection techniques, particularly for detecting AF.

Figure 5:
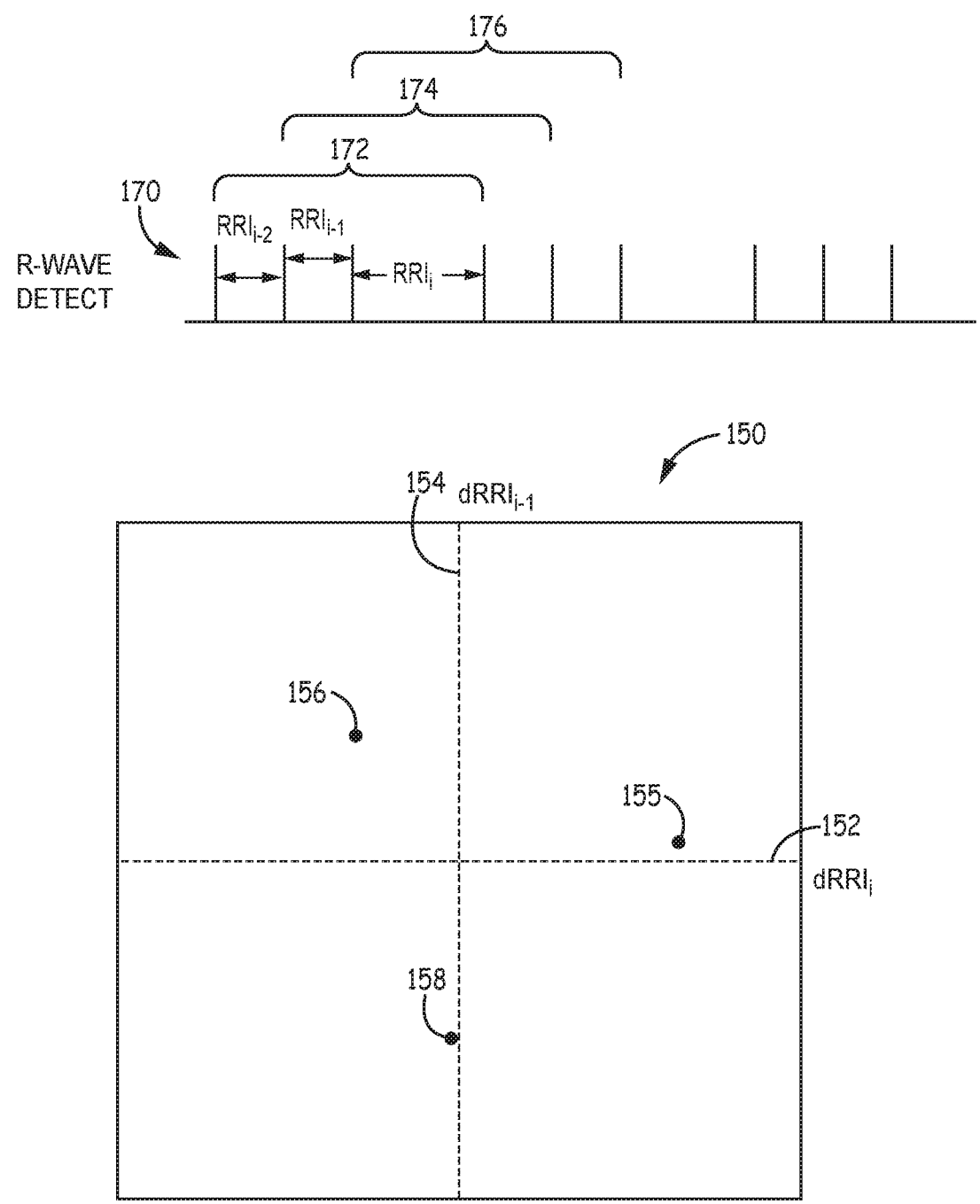
FIG. 5 is a schematic diagram of methods used for detecting cardiac events by any of the ICDs of FIGS. 1, 2A and 2B or the monitoring device of FIG. 3 according to one example.

FIG. 5 is a schematic diagram of methods used for detecting AF by a medical device, such as ICD 10, ICD 110. In order to determine whether AF is occurring, the microprocessor 224 (FIG. 4) may determine differences between RRIs based on sensed R-waves (e.g., R OUT signal line 202 in FIG. 4). Microprocessor 224 may make the decision as to whether an AF event is occurring based at least in part on the resulting pattern or signature of RRI differences. As described below, when the resulting signature of RRI differences acquired over a predetermined time period indicates AF is occurring, the cardiac signal time period is classified as AF. AF is detected when a required number of time periods are classified as AF. Techniques disclosed herein may be utilized as part of an overall tachyarrhythmia detection and discrimination algorithm implemented in ICD 10 or ICD 110 or the other devices described above or in other implantable or external cardiac devices.

The concept of using a signature of RRI differences for detecting AF is illustrated by the generation of a Lorenz scatter plot as shown in FIG. 5. Microprocessor 224 determines the differences between consecutive pairs of RR-intervals ($\delta$RRs) which can be plotted for a time series of RRIs. The Lorenz plot 150 is a Cartesian coordinate system defined by $\delta RR_i$ along the x-axis 152 and $\delta RR_{i-1}$ along the y-axis 154. $\delta RR_i$ is the difference between the $i^{th}$ RRI and the previous RRI, $RRI_{i-1}$. $\delta RR_{i-1}$ is the difference between $RRI_{i-1}$ and the previous RRI, $RRI_{i-2}$. As such, each plotted point in a Lorenz plot is defined by an x-coordinate equaling $\delta RR_i$ and a y-coordinate equaling $\delta RR_{i-1}$.

Each data point plotted on the Lorenz plot 150 represents an RRI pattern relating to three consecutive RRIs: $RRI_i$, $RRI_{i-1}$ and $RRI_{i-2}$, measured between four consecutively sensed R-waves 172. RRI information is not limited to detection of R-waves and determination of RRIs. The terms RRI and $\delta RR_i$ as used herein refer generally to a measurement of ventricular cycle length (VCL) and the difference between two consecutive VCL measurements, respectively, whether the VCL measurements were derived from a series of sensed R-waves from a cardiac electrical signal or a series of ventricular cycle event detections made from another physiological signal (e.g., a peak pressure determined from a pressure signal). For the sake of illustration, the methods described herein refer to R-wave detections for performing VCL measurements and the determination of ($\delta RR_i$, $\delta RR_{i-1}$) points.

As illustrated in FIG. 5, a series of R-waves 170 (represented by vertical bars) are sensed and in order to plot a point on the Lorenz plot area 150, a point is determined from the ordered pair ($\delta RR_i$, $\delta RR_{i-1}$) by determining successive RRIs determined from the sensed R-waves 170. In the example shown, a first series 172 of three consecutive RRIs ($RRI_{i-2}$, $RRI_{i-1}$ and $RRI_i$) provides the first data point 155 on the Lorenz plot area 150. $\delta RR_{i-1}$, which is the difference between $RRI_{i-2}$ and $RRI_{i-1}$ is near 0. $\delta RR_i$, the difference between the and $RRI_{i-1}$ and $RRI_i$, is a positive change. Accordingly, a ($\delta RR_i$, $\delta RR_{i-1}$) point 155 having a y-coordinate near 0 and a positive x-coordinate is plotted in the Lorenz plot 150, representing the first series 172 of four sensed R-waves (three RRIs).

The next series 174 of three RRIs provides the next ($\delta RR_i$, $\delta RR_{i-1}$) point 156 having a negative x-coordinate (the last RRI of series 174 being less than the immediately preceding RRI) and a positive y-coordinate (the middle RRI of series 174 being longer than the first RRI of series). This process of plotting ($\delta RR_i$, $\delta RR_{i-1}$) points continues with the three cycle series 176 providing data point 158 and so on.

Illustrative methods and devices for detecting AF using RRI differences determined from a ventricular cardiac electrical signal are generally described in commonly assigned U.S. patent application Ser. Nos. 14/520,798, 14/520,938 and 14/520,847 (Cao et al.), all of which are incorporated herein by reference in their entirety. An analysis of a Lorenz plot of the successive RRI differences may reveal an RRI variability pattern that is typical of AF. Other methods for detecting atrial tachyarrhythmias based on the irregularity of ventricular cycles determined from RRI differences that exhibit discriminatory signatures when plotted in a Lorenz scatter plot, such as the plot shown in FIG. 5, are generally disclosed by Ritscher et al. in U.S. Pat. No. 7,031,765; Sarkar, et al. in U.S. Pat. Nos. 7,623,911 and 7,537,569; and by Houben in U.S. Pat. No. 7,627,368, all of which patents are; incorporated herein by reference in their entirety.

Figure 6:
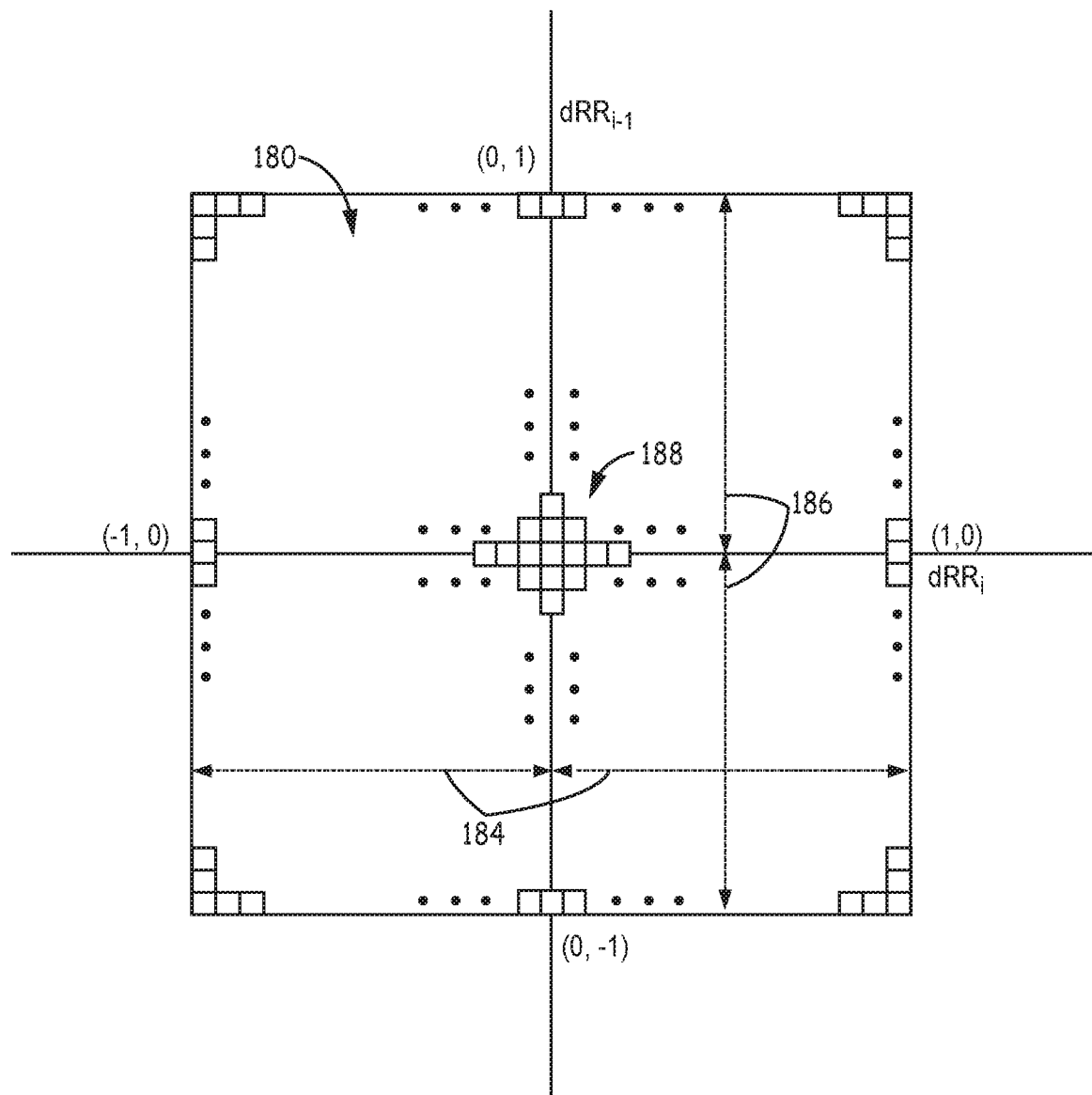
FIG. 6 is a diagram of a two-dimensional histogram representing a Lorenz plot area used in the techniques disclosed herein for detecting atrial tachyarrhythmia.

FIG. 6 is a diagram of a two-dimensional histogram representing a Lorenz plot area 150 used in the techniques disclosed herein for detecting atrial tachyarrhythmia. Generally, the Lorenz plot area 150 shown in FIG. 5 is numerically represented by a two-dimensional histogram 180 having predefined ranges 184 and 186 in both positive and negative directions for the $\delta RR_i$ coordinates (corresponding to x-axis) and $\delta RR_{i-1}$ coordinates (corresponding to y-axis), respectively. The two-dimensional histogram 180 is divided into bins 188 each having a predefined range of $\delta RR_i$ and $\delta RR_{i-1}$ values. In one example, the histogram range might extend from −1200 ms to +1200 ms for both $\delta RR_i$ and $\delta RR_{i-1}$ values, and the histogram range may be divided into bins extending for a range of 7.5 ms in each of the two dimensions resulting in a 160 bin×160 bin histogram 180. The successive RRI differences determined over a classification time period are used to populate the histogram 180. Each bin stores a count of the number of ($\delta RR_i$, $\delta RR_{i-1}$) data points falling into each respective bin range. The bin counts may then be used by microprocessor 224 in determining RRI variability metrics and patterns for detecting a cardiac rhythm type.

An RRI variability metric is determined from the histogram bin counts. Generally, the more histogram bins that are occupied, or the more sparse the distribution of ($\delta RR_i$, $\delta RR_{i-1}$) points, the more irregular the VCL is during the data acquisition time period. As such, one metric of the RRI variability that can be used for detecting AF, which is associated with highly irregular VCL, may take into account the number of histogram bins that have a count of at least one, which is referred to as an "occupied" bin. In one example, an RRI variability metric for detecting AF, referred to as an AF score, is determined by microprocessor 224 as generally described in the above-incorporated '911 patent. Briefly, the AF score may be defined by the equation:

AF Score=Irregularity Evidence−Origin Count−PAC Evidence wherein Irregularity Evidence is the number of occupied histogram bins outside a Zero Segment 188 defined around the origin of the Lorenz plot area. During normal sinus rhythm or highly organized atrial tachycardia, nearly all points will fall into the Zero Segment 188 because of relatively small, consistent differences between consecutive RRIs. A high number of occupied histogram bins outside the Zero segment 188 is therefore positive evidence for AF.

The Origin Count is the number of points in the Zero Segment 188 defined around the Lorenz plot origin. A high Origin Count indicates regular RRIs, a negative indicator of AF, and is therefore subtracted from the Irregularity Evidence term. In addition, a regular PAC evidence score may be computed as generally described in the above-incorporated '911 patent. The regular PAC evidence score is computed based on a cluster signature pattern of data points that is particularly associated with premature atrial contractions (PACs) that occur at regular coupling intervals and present regular patterns of RRIs, e.g., associated with bigeminy (short-short-long RRIs) or trigeminy (short-short-short-long RRIs). In other embodiments, the AF score and/or other RRI variability score for classifying an atrial rhythm may be determined by microprocessor 224 as described in any of the above-incorporated '765, '316, '911, '569 and '368 patents. Methods for rejecting noise in determining Lorenz plot points and an AF score are generally disclosed in U.S. Pat. No. 8,639,316 (Sarkar, et al.), incorporated herein by reference in its entirety. Methods for adjusting the AF score based on the presence of ectopy may be used in the techniques disclosed herein and are generally disclosed in U.S. Pat. No. 8,977,350 (Sarkar, et al.), incorporated herein by reference in its entirety. Other techniques that may be used in computing an AF score are generally disclosed in U.S. patent application Ser. Nos. 14/695,135, 14/695,156, 14/695,171 and 14/695,111 (Sarkar, et al.), all filed on Apr. 24, 2015 and incorporated herein by reference in their entirety.

The AF score is compared to an AF score threshold for classifying a predetermined time period of a cardiac signal as AF or non-AF based on the RRI analysis. The AF score threshold may be selected and optimized based on historical clinical data of selected patient populations or historical individual patient data, and the optimal AF score threshold setting may vary from patient to patient. In an illustrative example, the AF score may have a possible range of 0 to 100. The AF score threshold may be set between 25 and 75. If the AF score meets or crosses an AF score threshold, the time period over which the RRIs were collected, and thus the cardiac signal occurring within the time period, is classified as an AF time period. The AF score threshold may be adjusted after classifying at least one time period of the cardiac signal as being AF and the adjusted AF score threshold may be used for classifying subsequent time periods, which may lead to an AF detection. The adjusted AF score threshold is less than the initial AF score threshold and may have a value ranging from 19 to 57 in the example given above where the maximum AF score is 100 and the initial AF score threshold is at least 26 and not more than 75. Thus, the adjusted AF score threshold may be between 65-85% of the initial AF score threshold and, in some instances between 70-75% of the initial AF score.

An AF detection is made when a threshold number of detection time periods are classified as AF. In one example, a single n-second or n-minute time period classified as AF based on the AF score meeting the AF score threshold may result in an AF detection. In other examples, a higher number of time periods, e.g., three two-minute time periods for a total of 6 minutes of the cardiac electrical signal, may be required to be classified as being AF before detecting the heart rhythm as AF. As described below in conjunction with FIGS. 13-15, the threshold number of AF classified time periods required to detect AF may be automatically adjusted by microprocessor 224 based on the history of AF episodes detected in a given patient.

The microprocessor 224 provides a response to the AF detection, which may include withholding, adjusting or delivering a therapy (e.g., withholding ATP or shock therapy for treating a ventricular tachyarrhythmia or delivering an atrial anti-tachyarrhythmia therapy if available), storing cardiac signal data that can be later retrieved by a clinician using external device 40, triggering patient notification system 250, transmitting data via telemetry circuit 330 to alert a clinician, patient or caregiver, and/or triggering other signal acquisition or analysis.

The RRI analysis may continue to be performed by microprocessor 224 after an AF detection is made to fill the histogram during the next detection time period. After each detection time period, the AF score may be re-determined and the histogram bins are re-initialized to zero for the next detection time period. The new AF score (or other RRI variability metrics) determined at the end of each detection time period may be used to determine if the AF episode is sustained or terminated after the initial AF detection is made.

Figure 7:
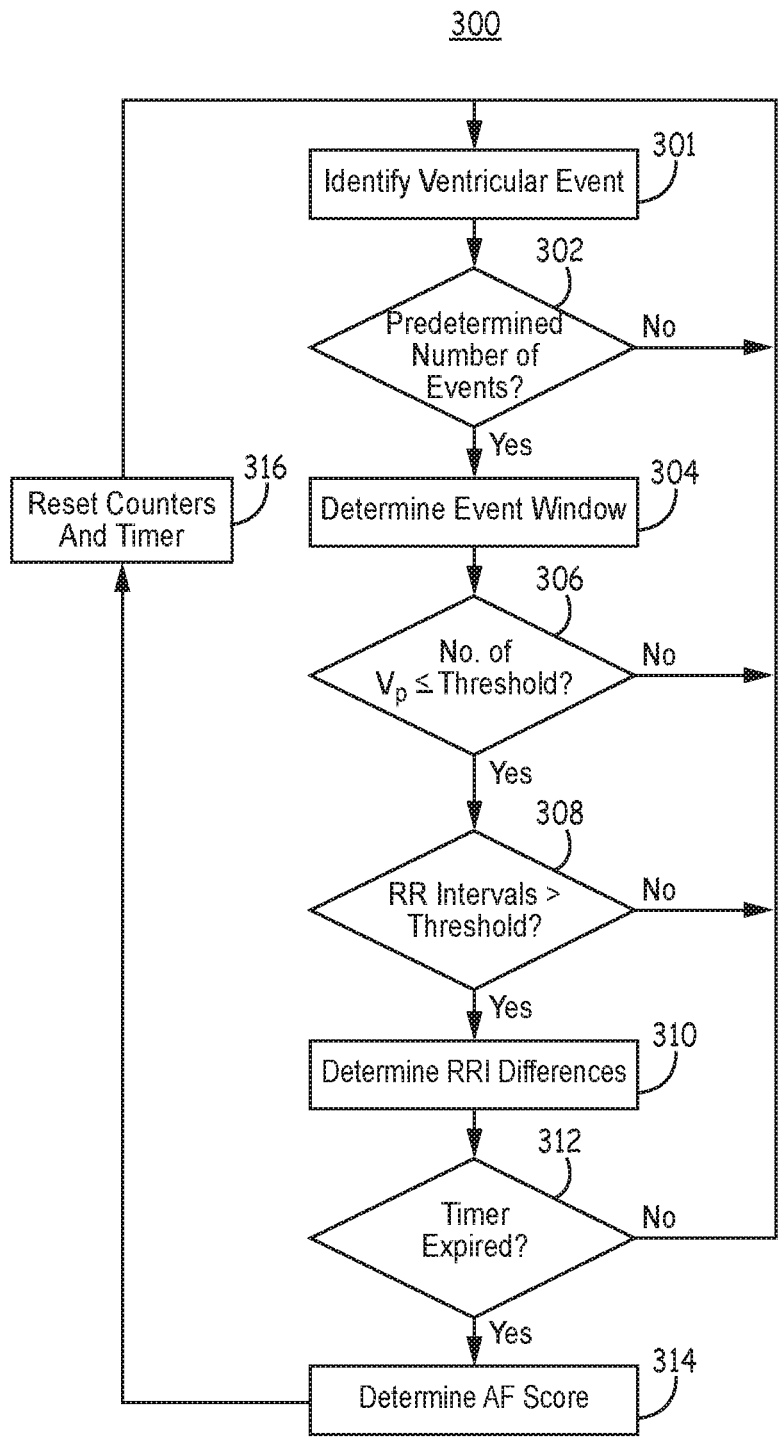
FIG. 7 is flowchart of a method for determining a factor for classifying time periods for detecting atrial tachyarrhythmia according to one example.

FIG. 7 is a flowchart 300 of a method for determining a factor for classifying time periods for detecting atrial arrhythmias according to one example. Flow chart 300 and other flow charts presented herein are intended to illustrate the functional operation of ICD 10 or another device performing the disclosed methods, and should not be construed as reflective of a specific form of software, firmware or hardware necessary to practice the methods. It is believed that the particular form of software, firmware and/or hardware will be determined primarily by the particular system architecture employed in the device and by the particular detection and therapy delivery methodologies employed by the device. Providing software, firmware and/or hardware to accomplish the techniques disclosed herein in the context of any modern medical device, given the disclosure herein, is within the abilities of one of skill in the art.

Methods described in conjunction with flow charts presented herein may be implemented in a non-transitory computer-readable medium that includes instructions for causing a programmable processor, such as microprocessor 224, to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

As illustrated in FIG. 7, the microprocessor 224 identifies ventricular events at block 301, such as R-waves based on Rout signal line 202, and identifies the ventricular event as being either an intrinsic sensed event Vs or a paced event Vp resulting from pacing being delivered by ICD 10 or 10' (or by ICD 110 or pacemaker 101). Depending upon the number of RR intervals chosen for determining RR interval differences, microprocessor 224 determines whether a predetermined number of events, either a ventricular pacing event Vp or intrinsic ventricular sensed event VS, have been identified at block 302. For example, according to one example, if the desired number of RR intervals for determining successive RR interval differences is three, the predetermined number of events utilized in block 302 would be four events, with the four events forming an event window. If the predetermined number of events has not been reached, "No" branch of block 302, microprocessor 224 determines the next ventricular event, at block 301, and the process is repeated.

Once the predetermined number of events are identified, "Yes" branch of block 302, an event window is identified based on the four events, at block 304, and a determination may be made as to whether the number of the events in the event window that are ventricular pace Vp events is less than or equal to a predetermined pacing event threshold at block 306. For example, according to one example, the pacing event threshold is set as one so that microprocessor 224 determines whether one or less of the identified events in the event window are ventricular pace events. If the number of identified events in the event window that are ventricular pace Vp events is not less than or equal to, i.e., is greater than, the predetermined pacing event threshold, "No" branch of block 306, microprocessor 224 identifies the next event at block 301, and the process is repeated.

If the number of events in the event window that are ventricular pace Vp events is less than or equal to the predetermined pacing event threshold, "Yes" branch of block 306, microprocessor 224 determines whether each of the RR intervals associated with the events in the current event window are greater than a predetermined interval threshold at block 308. For example, according to one example, microprocessor 224 determines whether each of the RR intervals associated with the events in the event window is greater than 220 milliseconds. If each of the RR intervals associated with the events in the event window are not greater than the predetermined interval threshold, "No" branch of block 308, microprocessor 224 identifies the next event at block 301, and the process is repeated using the next identified event and the resulting next event window.

If each of the RRIs associated with the events in the event window are greater than the predetermined interval threshold, "Yes" branch of block 308, microprocessor 224 determines differences between successive RRIs associated with the identified events in the event window, block 310. Once the RRI differences for the current event window have been determined at block 308, to populate a Lorenz plot histogram as described above, microprocessor 224 determines whether a predetermined time period has expired at block 312. Microprocessor 224 may set a timer or counter to control acquisition of RRI differences over a predetermined time period at the onset of the method of flow chart 300. In one example, the predetermined time period may be set to two minutes. If the time period has not expired, "No" branch of block 312, microprocessor 224 returns to block 301 to identify the next ventricular event and the process is repeated using the next event and the resulting next event window.

Once the timer has expired, "Yes" branch of block 312, microprocessor 224 determines an AF score at block 314, based on the determined RRI differences during the predetermined time period, e.g., two minutes. The AF score may be determined as described above with respect to FIG. 6 and/or the incorporated patents. As described below in conjunction with FIG. 8, the determined AF score for the predetermined time period is used to classify the time period (and thus the cardiac signal during the time period) as an AF time period, a non-AF time period or an unclassified time period. The stored RRI differences are then cleared and all counters and timers reset at block 316. A timer set to the predetermined time period, e.g., two minutes, is reset. Microprocessor 224 identifies the next ventricular event at block 300, and the process is repeated for the next time period using the next identified events and the next event windows.

Figure 8:
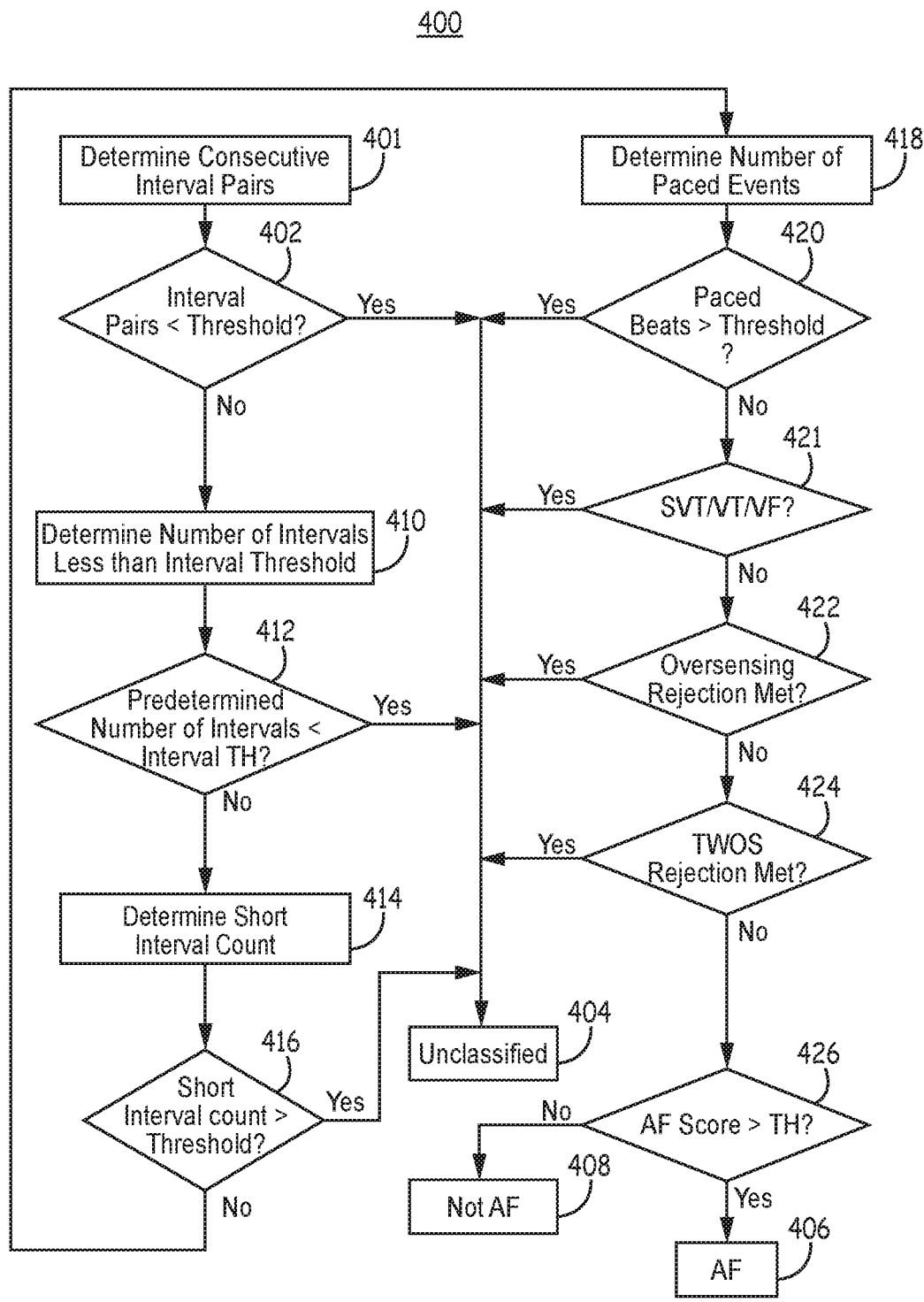
FIG. 8 is a flowchart of a method for classifying a predetermined time period for use in detecting atrial tachyarrhythmia according to one example.

FIG. 8 is a flowchart 400 of a method for classifying a predetermined time period according to one example. The example described in flowchart 400 of FIG. 7 will be described in the context of having predetermined time periods that are two minutes in length. However, the techniques described in FIG. 7 or elsewhere throughout this description can be for predetermined time periods that are longer or shorter than two minutes. Once the predetermined time period, e.g., a two-minute time period, has expired and a Lorenz plot has been populated with a point associated with ordered pairs representing each determined RR interval difference determined based on the intervals in each event window occurring during the two-minute time period as described in conjunction with FIGS. 5, 6 and 7, microprocessor 224 determines whether to classify the time period as being either an AF time period, a non-AF time period, or an unclassified time period (i.e., the time period can neither be classified as an AF time period nor a non-AF time period). For example, microprocessor 224 may analyze one or more of several factors, in any combination or particular order, to make the determination.

As described in conjunction with the example of FIG. 8, among the factors that may be analyzed for classifying the two-minute time period are the number of valid RRI difference pairs, RRI lengths, number of paced beats, number of short intervals, presence of oversensing of ventricular events, presence of T-wave oversensing, detection of a ventricular tachyarrhythmia (e.g., SVT, VT or VF or more generally referred to as "other episodes"), and the AF score. However, microprocessor 224 may analyze only a subset of these factors and/or include other factors.

Microprocessor 224 may determine the number of RRI difference pairs acquired during the two-minute time period at block 401, where each RRI difference pair represents one point of the Lorenz plot. A determination is then made as to whether the total number of RRI difference pairs formed during the two-minute time period is greater than an interval pair threshold at block 402. According to one example, a threshold number of RRI difference pairs is set at 30, though other thresholds may be used. If the total number of RRI difference pairs (representing three consecutive RRIs) during the two-minute time period is less than the threshold, "Yes" branch at block 402, the two-minute time period is determined to be unclassified at block 404. In the example described above in which the threshold is set at 30, the "Yes" branch of block 402 means that less than 30 RRI difference pairs were determined during the two-minute time period, resulting in the Lorenz plot histogram being populated with less than 30 points. An AF score determined from fewer than the threshold number of RRI difference pairs may not yield a reliable AF score for the predetermined time period and therefore is not used to classify the time period as either AF or non-AF.

If the number of RRI difference pairs that are formed during the two-minute time period is not less than the interval pair threshold (30 in the example above), "No" branch of block 402, the interval pairs factor for classifying the time period as either AF or non-AF based on an AF score determined from the RRI difference pairs is satisfied. In other words, using the example above, 30 or RRI difference pairs were determined during the two-minute time period, resulting in the Lorenz plot histogram being populated with 30 or more points. The number of RRI difference pairs obtained during the pre-determined time period is adequate to reliably classify the time period as AF or non-AF based on the AF score.

According to another example, microprocessor 224 may additionally or alternatively determine, at block 410, the total number of RRIs during the predetermined time period that were determined to be less than the interval threshold applied at block 308 of flow chart 300. If more than a threshold number of RRIs, e.g., more than a predetermined number of RRIs or a predetermined percentage of the total number of RRIs occurring during the two-minute time period, are less than the interval threshold, "Yes" branch at block 412, the two-minute time period is determined to be unclassified, at block 404. If the number of RRIs less than the interval threshold does not reach or exceed a predetermined number, e.g., if less than 10 RRIs are less than the interval threshold during the two-minute time period, this RRI length factor is determined not to be satisfied at block 412 ("No" branch of block 412) for classifying the predetermined time interval as unclassified. Based on at least this factor, a classification of either AF or non-AF based on the AF score is warranted.

In order to classify the two-minute time period as either AF or non-AF, microprocessor 224 may determine, at block 414, a short interval count of the total number of RRIs from all of the event windows obtained during the two-minute time period that were less than or equal to a predetermined short interval threshold, such as 120 milliseconds or 130 milliseconds, for example. Microprocessor 224 determines whether the short interval count is greater than a short interval threshold, at block 416, such as 5 short intervals for example. Too many short intervals during the two-minute time period indicates the possibility of ventricular oversensing of non-physiological signals such as EMI or lead noise due to lead fracture. In this situation, the RRIs may be unreliable for determining an AF score and classifying the time period as AF or non-AF based on the AF score.

If the determined short interval count is greater than the short interval count threshold, "Yes" branch at block 416, the two-minute time period is determined to be unclassified at block 404. On the other hand, if the short interval count is less than the short interval count threshold, the time period can be classified based on the AF score, "No" branch at block 416. This short interval count factor minimizes false AF detection due to lead noise oversensing.

Microprocessor 224 may additionally or alternatively determine the number of events identified during the total two-minute time period within all of the event windows that were determined to be ventricular pace Vp events at block 418. A determination is made as to whether the determined number of ventricular pace Vp events identified during all event windows of the two-minute time period is greater than a total ventricular pace Vp event threshold at block 420. According to one example, the total ventricular pace Vp threshold is set as 30 ventricular pace Vp events, though other thresholds may be used.

If the number of ventricular pace Vp events during the two-minute time period is greater than the total ventricular pace Vp event threshold, "Yes" branch of block 420, microprocessor 224 classifies the two-minute time period as unclassified at block 404. Ventricular pacing pulses may include bradycardia pacing pulses and/or ATP pacing pulses and may be delivered by ICD 10 or 110 or by another implanted device, e.g., pacemaker 110. On the other hand, if the determined number of ventricular pace Vp events is not greater than Vp event threshold, "No" branch at block 420, the two-minute time period is not classified as unclassified; a classification of AF or non-AF based on the AF score may be made as long as no other factors lead to a determination of the time period being unclassified.

Microprocessor 224 may be configured to simultaneously evaluate R-waves and RRIs for detecting supraventricular tachycardia (SVT), VT and VF while the AF detection algorithms described herein are operating. ICD 10 may be configured to deliver therapies such as ATP in response to detecting VT. As such, if a ventricular tachyarrhythmia detection, e.g., SVT, VT or VF detection, is being made during or at the expiration of the current time period, as determined at block 421, the current time period is determined to be unclassified at block 404. If no other episode detections are being made, the process may advance to block 422.

The microprocessor 224 may additionally or alternatively determine whether ventricular event oversensing caused by noise was detected during the two-minute time period, at block 422. Detection of oversensing may be performed by microprocessor 224 using an implemented oversensing detection scheme, such as the oversensing detection methods generally described in U.S. Pat. No. 7,333,855 to Gunderson et. al., incorporated herein by reference in its entirety. If oversensing detection criteria were met or were in the process of being met during the two-minute time period, "Yes" branch of block 422, the two-minute time period is determined to be unclassified at block 404. Detection of oversensing indicates that the RRIs may be unreliable for determining an AF score and classifying the time period based on the AF score. If a detection of oversensing was not made or not in the process of being made during the two-minute time period, "No" branch of block 422, an AF or non-AF classification may be made based on the AF score as long as other factors do not lead to the time period be classified as unclassified.

Microprocessor 224 may determine whether T-wave oversensing occurred during the two-minute time period at block 424. The determination of T-wave oversensing may be performed by ICD 10 using an implemented T-wave oversensing detection scheme, such as the T-wave oversensing determination described in U.S. Pat. No. 7,831,304 (Cao, et al.), incorporated herein by reference in its entirety. If a determination of T-wave oversensing was made or was in process during the two-minute time period, "Yes" branch of block 424, the T-wave oversensing factor is satisfied as an indication of the two-minute time period being unclassified. Microprocessor 224 classifies the two-minute time period as unclassified at block 404. If a determination of T-wave oversensing was not made or was not in the process of being made during the two-minute time period, "No" branch of block 424, the T-wave oversensing factor is not satisfied. Microprocessor 224 advances to block 426 to classify the time period based on the AF score.

In this way, ICD 10 or ICD 110 may analyze the cardiac electrical signal over the two-minute time period for one or more of the described factors, which if satisfied would cause the two-minute time period to be classified as "unclassified." In other words, ICD 10 or 110 may analyze all of the described factors or only a subset of the described factors in making this determination. In some examples, if at least one the described factors for identifying the two-minute time period as being unclassified is met, the two-minute time period is classified as unclassified at block 404. If none of the factors evaluated in blocks 401 through 424 are determined to be satisfied according to predetermined criteria, the time period is classified as either AF or non-AF based on the AF score. As such, the AF score is determined based on the populated Lorenz plot histogram as described above. If the AF score is greater than an AF threshold at block 426, the two-minute time period is classified as AF at block 406. On the other hand, if the AF score is not greater than the AF threshold, "No" branch of block 426, the two-minute time period is classified as a non-AF at block 408.

It is understood that the determination of whether the time period is classified as unclassified (block 404), classified as AF (block 406), or classified as non-AF (block 408), may be made in any order, or at the same time, so that the determination of the two-minute time period as being an unclassified time period may be used to override an initial determination of the two-minute time period as being classified as AF or non-AF, or be made prior to determining the AF score for making a classification based on the AF score.

Figure 9:
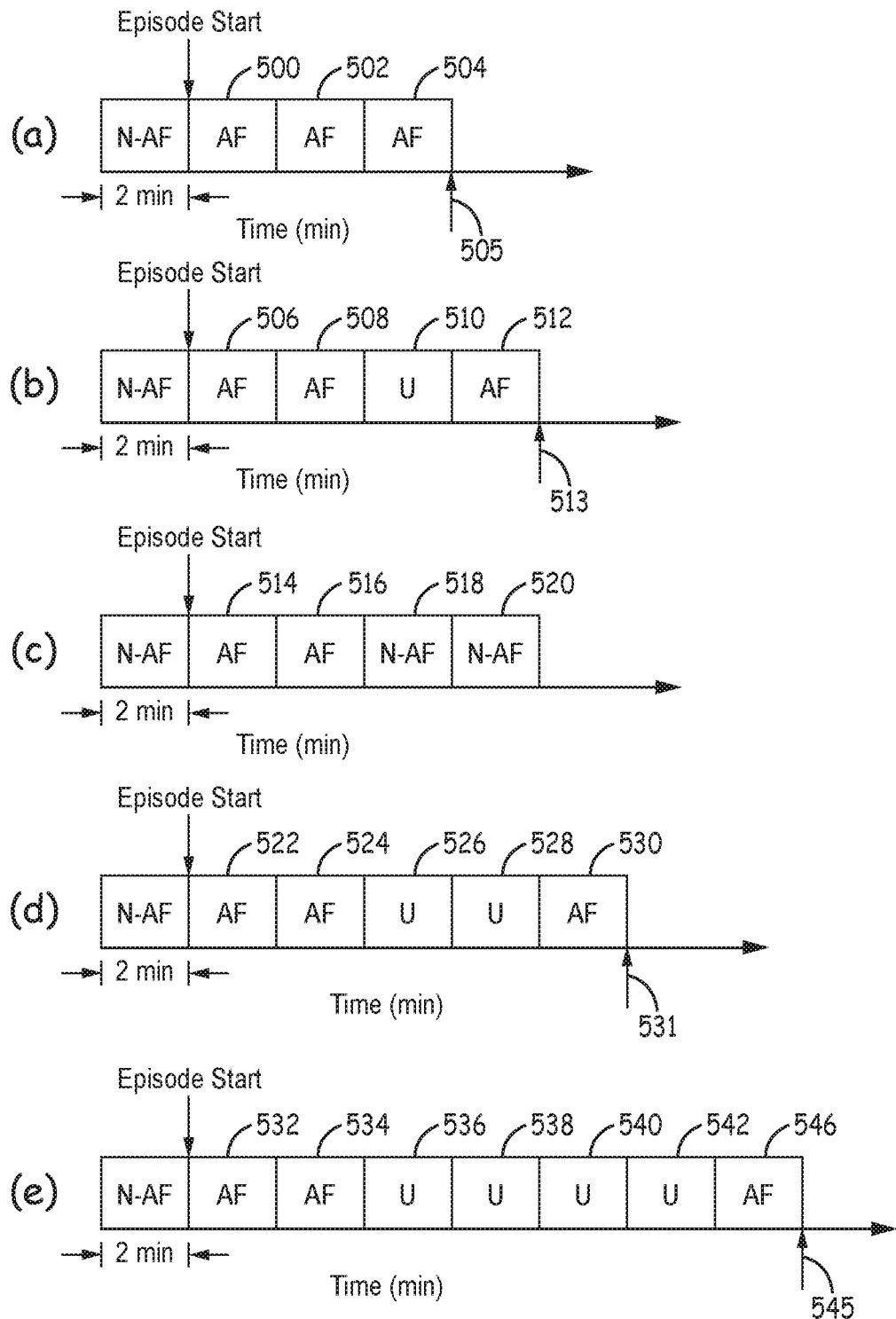
FIG. 9 is a schematic diagram of atrial fibrillation detection that may be performed by the ICDs shown in FIGS. 1, 2A and 2B or the monitor of FIG. 3.

FIG. 9 is a schematic diagram of atrial fibrillation detection that may be performed by a medical device according to one example. The examples described in FIG. 9 will be described in the context of classifying predetermined time periods that are two minutes in length. However, the techniques described in FIG. 9 can be implemented by classifying predetermined time periods that are longer or shorter than two minutes.

As illustrated in FIG. 9, the microprocessor 224 classifies the cardiac signal of each two-minute time period as being either AF, non-AF or unclassified using the method described in conjunction with FIG. 7. The classifications of the time periods are used to detect an AF episode. For example, once a predetermined number of two-minute time periods, such as three time periods, have been classified as AF, the device detects the AF episode. Therefore, as illustrated in the scenario of timing diagram (a) of FIG. 8, once the predetermined number of two-minute time periods, 500, 502 and 504, are classified as AF, microprocessor 224 detects the AF episode at time 505. The microprocessor 224 may track the number of two-minute time periods classified as AF by updating an AF event counter each time a time period is classified as AF.

However, in the scenario illustrated in timing diagram (b), two consecutive two-minute time periods 506 and 508 are classified as being AF, but the next two-minute time period 510 is determined to be unclassified, followed by a subsequent time period 512 being classified as AF. According to one example, microprocessor 224 may ignore the unclassified two-minute time period 510 and detect an AF episode at time 513 once the third time period 512 is classified as AF, so that an AF episode may be detected despite one or more unclassified time periods occurring between time periods classified as AF.

In the timing diagram of scenario (b), at the identification of two-minute time period 506, an AF event counter may be incremented to one. At the identification of subsequent two minute period 508, the AF event counter is incremented to two. At the classification of subsequent two-minute time period 510, since the cardiac signal was determined to be unclassified, the AF event counter remains at a count of two. At the classification of subsequent two-minute time period 512, the AF event counter is incremented to three, and an AF episode is detected in response to the AF event counter reaching the AF detection threshold, which is 3 in this example.

As illustrated in the timing diagram of scenario (c), the classification of one or more time periods as non-AF result in no detection of an AF episode. During the determination of whether the predetermined number of two-minute time periods are classified as AF, the microprocessor 224 updates the AF event counter each time an AF classification is made as described above. For example, upon classification of two-minute time period 514, the AF event counter is incremented to one, and at the classification of subsequent two-minute time period 516, the AF event counter is incremented to two. If two-minute time period 518 were also classified as AF, microprocessor 224 would detect an AF episode, since three two-minute time periods classified as AF would have occurred, e.g., as described in the timing diagram of scenario (a) above. However, since two-minute time period 518 is classified as non-AF, an AF episode detection is not made. The non-AF classification of time period 518 may be evidence that an AF episode causing AF classifications of time periods 514 and 516 is terminated or a non-sustained AF episode. In response to classifying time period 518 as non-AF, the AF event counter is reset to zero. In other examples, the AF counter may be decreased when a time period is classified as non-AF rather than immediately reset to zero.

In the timing diagram of scenario (d), at the classification of two-minute time period 522 as being AF, the AF event counter is incremented to one, and at the classification of subsequent two-minute time period 524 as AF, the AF event counter is incremented to two. At the classifications of subsequent two-minute time periods 526 and 528, both determined to be unclassified, the AF event counter remains unchanged at a count of two. Upon classification of subsequent two-minute time period 530 as being AF, the AF event counter is increased to three, and an AF episode is detected at time 531.

Had any of time periods 524, 526, 528 or 530 been classified as non-AF, the AF event counter would have been reset to zero, and the process repeated starting with the next classified two-minute time period. However, in addition to resetting the AF event counter in response to a two-minute time period being classified as a non-AF time period, microprocessor 224 may also be configured to reset the AF event counter to zero if a predetermined number of two-minute time periods are determined to be unclassified. For example, five consecutive two-minute time periods determined to be unclassified may cause the AF event counter to be reset to zero. In other examples, more than five or fewer than five unclassified time periods, which may not be required to be consecutive, may cause the AF counter to be decremented or reset to zero. Therefore, in the timing diagram of scenario (e), at the identification of two-minute time period 532 as AF, the AF event counter is incremented to one. At the identification of subsequent two-minute time period 534 as AF, the AF event counter is incremented to two. At the identification of the four subsequent two-minute time periods 536, 538, 540 and 542, all determined to be unclassified, the AF event count remains unchanged at two. In the example shown, the next two-minute time period 546 is classified as AF. The AF event counter is incremented from two to three, and an AF episode is detected at 545 by microprocessor 224 in response to the AF event counter reaching the threshold count, which is three in this example.

On the other hand, if the subsequent two-minute time period 546 had been determined to be unclassified, the AF event counter would be reset to zero in response to a threshold number (five in this example) of consecutive unclassified time periods. If time period 546 had been classified as a non-AF time period, the AF event counter would also be reset to zero. In either of these two cases, if the time periods 532 and 534 represent a true AF episode, the AF episode has terminated or is non-sustained as evidenced by the unclassified and/or non-AF classified time periods. The process is repeated starting with the next classified two minute interval.

Figure 10:
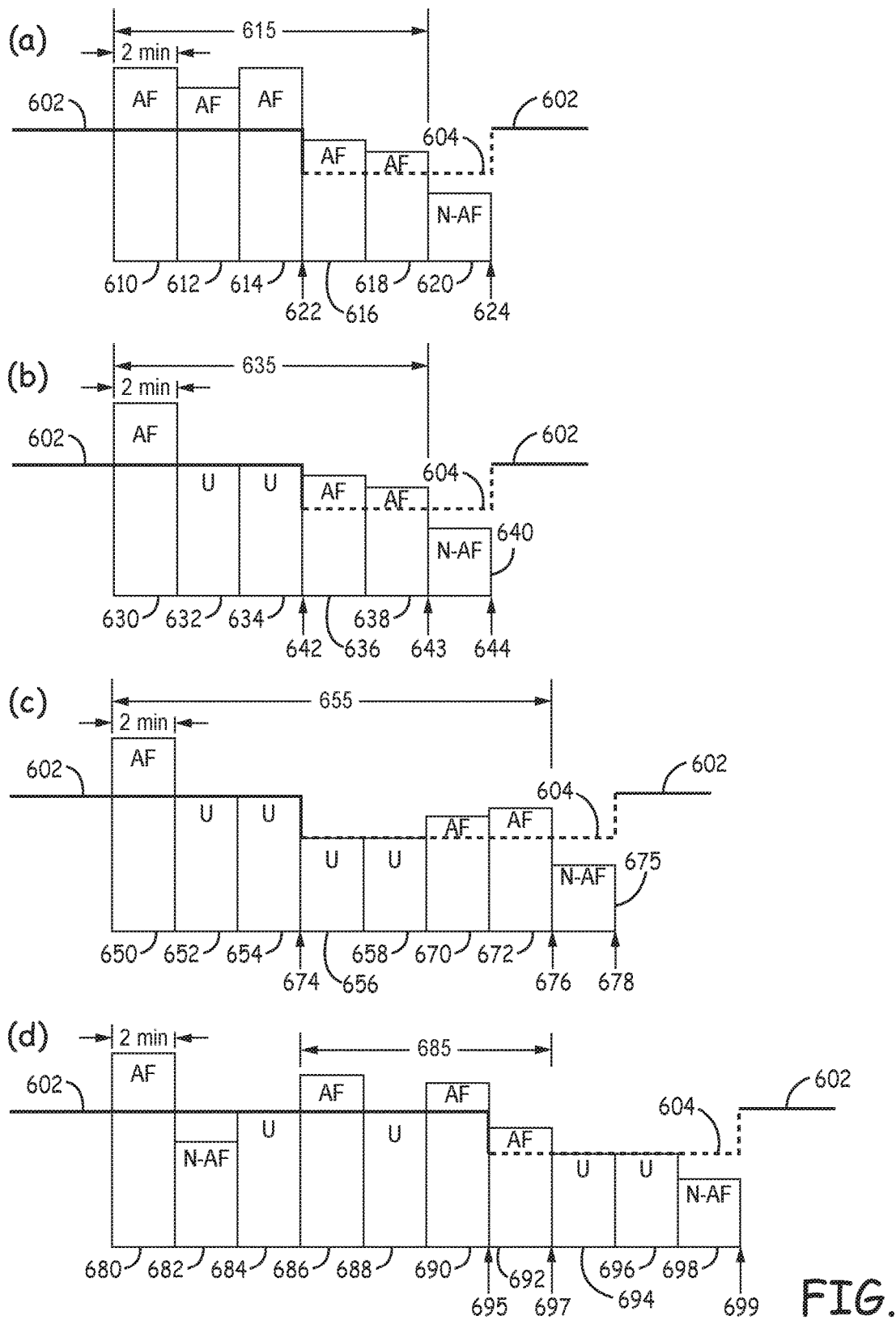
FIG. 10 is a schematic diagram of a method for detecting atrial fibrillation by an ICD or implantable monitoring device according to another example.

FIG. 10 is a schematic diagram of a method for detecting atrial fibrillation that may be performed by ICD 10 or ICD 110 (or cardiac monitoring device 60) according to another example. The examples described in FIG. 10 will be described in the context of having predetermined time periods that are two minutes in length and an AF detection threshold set equal to 3 time periods classified as AF. However, the techniques described may utilize different time period durations and/or different thresholds. As described below in conjunction with FIGS. 13-15, the threshold number of time periods, or total time duration of the cardiac signal required to be classified as AF may be automatically adjusted by microprocessor 224.

The microprocessor 224 classifies the cardiac signal within each two-minute time period as being either AF, non-AF or unclassified using the method described in conjunction with FIG. 8. If factors that cause the two-minute time period to be unclassified are not satisfied, each two-minute time period is classified as AF or non-AF based on the AF score. In the method of FIG. 10, the threshold that the AF score is compared to for classifying a time period is not a fixed value but is dynamically adjusted by microprocessor 224 in response to classifications of two-minute time periods.

For example, once a predetermined number of time periods, such as one time period, has been classified as AF based on a first AF score threshold value, if the next predetermined number of time periods are classified as any combination of AF and/or unclassified, the AF score threshold is adjusted to a second, lower value. In other words, following an initial AF classification using the first, higher AF score threshold, microprocessor 224 decreases the AF score threshold to the second lower value at the expiration of a predetermined number of next consecutive time periods, e.g., two consecutive time periods following the initial AF classification in the examples illustrated in FIG. 9, as long as none of the predetermined number of next consecutive time periods are classified as non-AF. In other instances, the predetermined number of next consecutive time periods may be less than two, e.g., zero or one, or more than two. If any of the predetermined number of next consecutive time periods following an initial AF classification are classified as non-AF, the AF score threshold remains at the first higher threshold value.

Therefore, as illustrated in the scenario of timing diagram (a) of FIG. 10, an initial time period 610 is classified as AF based on the AF score determined for time period 610 being greater than a first AF score threshold 602 and analysis of other classification factors does not lead to an unclassified time period (as described with FIG. 8). The first AF score threshold 602 stays in effect for at least two more consecutive time periods 612 and 614 in this example. If both of these time periods are also classified as AF, in response to an AF score exceeding the first AF score threshold 602, AF is detected at time 622. Additionally, microprocessor 224 adjusts the AF score threshold to a second, lower AF score threshold 604 at time 622. The AF score of subsequent time periods will be compared to this lower threshold 604 for classifying the respective time periods.

The lower AF score threshold 604 may be set to a percentage of the initial AF score threshold 602, e.g., approximately 75% of the initial AF score. To illustrate, when the maximum possible value of the AF score is 100, the first AF score threshold may be set at 75 and adjusted to a second, lower AF score of 57. In another example, the first AF score threshold is 60 and the second is 45. In still other examples, the first AF score threshold is 60 and the second is 45, the first is 50 and the second is 38, the first is 40 and the second is 30, or the first is 25 and the second is 19. A user may program the AF score thresholds based on selection of a least sensitive, e.g., first threshold of 75 and second threshold of 57, to most sensitive, e.g., first threshold 25 and second threshold 19, with the other example given above corresponding to a less sensitive setting (first threshold 60 and second threshold 45), balanced sensitivity (first threshold 50 and second threshold 38), and more sensitivity (first threshold 40 and second threshold 30). In other examples, the actual values of the first and second thresholds may be programmable selected individually in any combination of a first range, e.g., from 25 to and including 75 for the first threshold, and a second range, e.g., from 19 to and including 57 for the second threshold, as long as the first threshold is greater than the second threshold value. In other examples, the second threshold may be set to be another percentage of the initial threshold, e.g., between 65-85%, 70-80%, or some other percentage.

By reducing the AF score for subsequent time periods, AF detection sensitivity is increased at appropriate times. AF detection specificity is maintained by using the first higher AF score threshold and applying the factors that lead to unclassified time periods. For example, the next two consecutive time periods 616 and 618 are both classified as AF based on an AF score exceeding the second threshold 604, even though the first, higher threshold 602 is not met (and factors leading to an unclassified classification are not present). The AF episode is detected as still being in progress during time periods 616 and 618 even though the AF scores for these time periods 616 and 618 are each less than the first threshold 602. The next time period 620 is classified as non-AF due to an AF score being less than the second threshold 604. In response to the non-AF classification, microprocessor 224 adjusts the AF score threshold from the lower threshold 604 back to the higher threshold 602 at time 624. Termination of the AF episode is detected in response to the non-AF classification. The AF episode duration 615 is the time interval from the start of the earliest time period 610 classified as AF that led to AF detection at time 622 to the end of last AF classification time period 618 that precedes termination detection at time 624, i.e., that precedes the time period 620 classified as non-AF.

In the scenario illustrated in timing diagram (b), two consecutive two-minute time periods 632 and 634 are determined to be unclassified after an initial time period 630 that is classified as AF based on the first AF score threshold 602. In response to neither of the two time periods 632 and 634 being classified as non-AF following the initial AF classification of time period 630, microprocessor 224 adjusts the AF score threshold at time 642 to the second lower threshold 604. Three consecutive classifications including at least an initial AF classification and no non-AF classifications cause an adjustment of the AF score threshold. As such, in one example, time periods 632 and 634 immediately and consecutively following the initial AF classified time period 630 may both be unclassified (as shown in this example), both be classified as AF, or one classified as AF and one unclassified to cause the AF score threshold to be adjusted at time 642.

Since only one time period 630 has been classified as AF in the example shown, however, an AF detection is not made at time 642 when the AF score threshold is adjusted. The next two time periods 636 and 638 are classified as AF in response to an AF score being greater than the adjusted AF score threshold 604 (and factors that would cause an unclassified classification to be made not being identified). When the AF event counter reaches a count of three at time 643, an AF detection is made. The next time period 640 is classified as non-AF in this example. Termination of the AF episode is detected, and the AF score threshold is adjusted from the lower value 604 back up to the higher value 602 at time 644 in response to the non-AF classification and resulting episode termination detection.

The episode duration 635 starts with the earliest time period 630 that was classified as AF and led to AF detection at time 643 and extends through the latest AF-classified time period 638 prior to termination detection at time 644. The episode duration 635 includes unclassified time periods 632 and 634 that do not lead to detection of termination at time 644. Unclassified time periods 632 and 634 occur between AF-classified time periods 630 and 636 and are therefore included in AF episode duration 635. The time periods 632 and 634 may be classified as unclassified due to any of the other factors described in FIG. 8. In one particular example, one or both of the time periods 632 and 634 may be unclassified due to ventricular tachyarrhythmia detection (block 421 of FIG. 8). By allowing time periods 632 and 634 to be classified as unclassified when ventricular tachyarrhythmia is being detected, the detection of AF and determination of the AF episode duration 635 are uninterrupted. The detection of an AF episode that is concurrent with a ventricular tachyarrhythmia episode provides important diagnostic information for the clinician to use in properly determining the patient's heart rhythm status and subsequent treatment.

In scenario (b) and other scenarios that follow, the time periods determined to be unclassified, e.g., time periods 632 and 634 are represented as having AF scores being equal to the currently set AF score threshold. It is to be understood, however, that an actual AF score, if determined, may be greater than, equal to, or less than the current value of the AF score threshold but is not used to classify the time period when the analysis of other factors cause the time period to be determined as unclassified as described in conjunction with FIG. 8. In some cases, if the time period is determined to be unclassified due to analysis of one or more factors as described in conjunction with FIG. 8, determination of an AF score for the current time period may not be made; classification of the time period as unclassified may preclude the need to determine the AF score in some examples.

In scenario (c), the AF score threshold is adjusted from a first threshold 602 to a second threshold 604 at time 674 after an initial AF classified time period 650 based on the first, higher threshold 602 followed by two consecutive time periods 652 and 654 that do not include a non-AF classification. Microprocessor 224 may increment an AF event counter in response to each AF classification and increment an unclassified event counter in response to each unclassified time period. Accordingly, in the example of scenario (c), at time 674 the AF event counter is at a count of one, and the unclassified event counter is at a count of two. After time period 656, the unclassified event counter is at a count of three, and after time period 658 the unclassified event counter is at a count of four. The next two time periods 670 and 672 are classified as AF based on the respective AF scores exceeding the second, lower AF score threshold 604. If the next time period 670 is also an unclassified time period, such that five unclassified time periods occur consecutively, the AF event counter and the unclassified event counter may be reset to zero, and the AF score threshold may be increased to the first, higher AF score threshold 602. Microprocessor 224 may therefore adjust the AF score threshold and reset counters in response to detecting a predetermined number of consecutive unclassified time periods.

In the example shown, the next time period 670 is classified as AF so the unclassified event counter remains at a count of four. The AF event counter is increased to two after time period 670 and to three after time period 672. AF is detected at time 676 in response to the AF event count reaching the detection threshold, which is three in this example. The AF score threshold remains at the second, lower threshold 604 until termination of the AF episode is detected in response to a non-AF classification, e.g., time period 675, or a predetermined number of consecutive unclassified time periods, e.g., five consecutive unclassified time periods. At time 678, the AF score threshold is adjusted to the first, higher threshold 602 in response to the non-AF classification of time period 675. As shown by the example of scenarios (b) and (c), an AF episode may be detected after the AF threshold is adjusted to the second, lower threshold.

The episode duration 655 in scenario (c) begins with AF time period 650 and extends through AF time period 672 which led to AF detection at time 676. This episode duration 655 includes the consecutive unclassified time periods 652, 654, 656, and 658 which do not lead to detection of AF termination at 678.

Scenario (d) shows another example of a series of two-minute time period classifications and the corresponding adjustment to the AF score threshold. An initial time period 680 is classified as AF based on the first, higher AF score threshold 602. The AF event counter is increased to a count of one. The next time period 682 is classified as non-AF based on the first AF score threshold 604. The AF event counter may be reset to zero in response to the non-AF classification. The unclassified time period 684 may not be counted by microprocessor 224 since the AF event counter is currently zero.

A subsequent sequence of AF-U-AF (time periods 686, 688 and 690, respectively) result in an AF event count of two and an unclassified event count of one. The two consecutive time periods 688 and 690, following the AF time period 686 and classified as unclassified and AF, respectively, result in a combined event count of the AF and unclassified time periods being equal to three. In response to this combined event count of three, microprocessor 224 adjusts the AF score threshold from the first, higher AF score threshold 602 to the second lower AF score threshold 604 at time 695. AF is not yet detected because the AF event count is two. The next time period 692 is classified as AF based on a comparison of the AF score to the second, lower AF score threshold 604. Microprocessor 224 increases the AF event count to three and detects AF at time 697 in response to the AF event count reaching the detection threshold. Upon detecting AF at time 697, the unclassified event counter is reset to zero. The unclassified event counter will count unclassified time segments beginning from zero after the AF detection in order to count consecutive unclassified time periods for detecting termination of the AF episode. The unclassified event count reaches two after time periods 694 and 696. The next time period 698 is classified as non-AF resulting in detecting termination of the AF episode at time 699. All event counters are reset to zero, and the AF score threshold is adjusted back to the first, higher threshold 602 at time 699.

The episode duration 685 starts with AF-classified time period 686 which is the earliest AF classified episode that led to AF detection at time 697. The episode duration includes unclassified time period 688 which did not contribute to detection of termination at block 699. Episode duration 685 ends with the last AF-classified time period 692 prior to detecting termination at time 699. Unclassified time periods 694 and 696 may, in some instances, not be included in the episode duration 685 because they immediately precede the non-AF classified time period 698 that results in episode termination detection with no intervening AF-classified episode. In other instances, however, those unclassified time periods may also be included in the episode duration 685.

The first and second AF score thresholds 602 and 604 may be fixed values or may be programmable by a user. In one example, a user may program the first and second AF score thresholds 602 and 604 to be increased or set to relatively higher respective values than currently programmed values or decreased or set to relatively lower values than the currently programmed values. Both the first and second AF score thresholds are adjusted together up or down by the same increment or decrement respectively, in response to the user-entered programming command. In other examples, a user may programmably select each of the first and second AF score thresholds tailored to individual patient need.

While only two different AF score thresholds 602 and 604 are illustrated in the example of FIG. 10, it is understood that the AF score threshold may be adjusted between three or more AF score threshold values in other examples. For instance, after AF detection is made at time 697, the AF score threshold set to the second, lower threshold 604 could be reduced to a third lowest AF score threshold to allow continuing detection of the AF episode using less stringent criteria than the initial AF detection criteria. In other examples, once the AF detection is made at time 697, the AF score threshold could be increased from the second, lower threshold 604 back up to the first, higher threshold 602 or to a third, intermediate threshold value between the second, lower threshold 604 and the first, higher threshold 602. The third intermediate threshold value may be applied for classifying subsequent time periods until termination of the AF episode is detected based on a predetermined number of time periods being classified as non-AF based on an AF score falling below the third intermediate threshold value.

In the example scenarios of FIG. 10, the AF score threshold is adjusted after at least two consecutive time period classifications of any combination of AF and unclassified immediately follow a preceding or initial AF classified time period. In other examples, the AF score threshold may be adjusted after fewer or more time periods. For example, a single time period classified as AF may cause the AF score threshold to be reduced to a second lower value. In other examples, at least one unclassified or AF time period following an immediately preceding AF time period may cause the AF score threshold to be adjusted. In still other examples, more than two time periods that are not classified as non-AF and consecutively follow a first time period classified as AF may be required before adjusting the AF score threshold.

Figure 11:
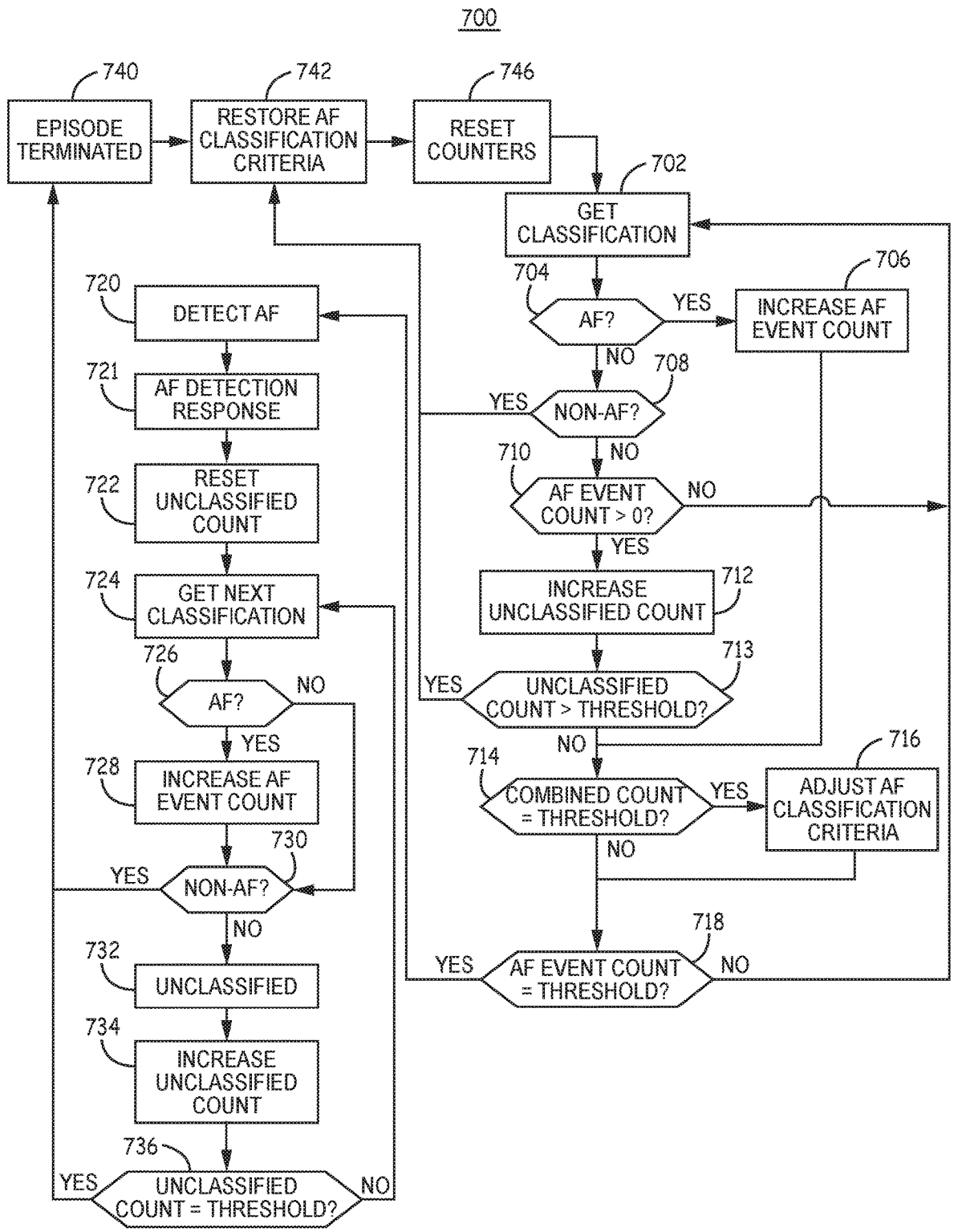
FIG. 11 is a flowchart of a method for detecting atrial fibrillation, according to one example.

FIG. 11 is a flowchart 700 of a method for detecting atrial fibrillation, according to one example. At block 702, the classification of the current time period is determined. If the classification is AF, as determined at block 704, microprocessor 224 increases the AF event counter at block 706 and advances to block 714 to compare a combined count of the AF event counter and the unclassified event counter to a threshold. If the combined counts do not meet the threshold at block 714, the AF event count is compared to the AF detection threshold at block 718. If the AF detection threshold is not reached, the process returns to block 702 to get the next time period classification.

If the time period is not classified as AF, "No" branch of block 704, and is classified as non-AF, "Yes" branch of block 708, the microprocessor 224 advances to block 742. The AF classification criteria, if previously adjusted, are restored to initial values. For example, if an AF score threshold has been previously adjusted to a second lower threshold, the AF score threshold is returned to a higher first threshold as described in conjunction with FIG. 10. At block 746, the AF event counter and the unclassified event counter are reset to zero if they have been previously incremented to a non-zero value.

If the current time period classification obtained at block 702 is neither AF nor non-AF, i.e., if the current time period is determined to be unclassified, "No" branch of block 708, and the AF counter is currently inactive with a value of zero, "No" branch of block 710, microprocessor 224 determines the classification of the next time period at block 702. If the AF event count is greater than zero as determined at block 710, indicating that an initial AF classification has been made, and the current time period is unclassified, microprocessor 224 increases the unclassified event count by one at block 712. The unclassified event count may be used for controlling adjustment of AF classification criteria prior to an AF detection being made as described in conjunction with FIG. 10. If the unclassified event count has reached a predetermined threshold, "Yes" branch of block 713, microprocessor may restore initial AF classification criteria (if previously adjusted) at block 742 and reset the unclassified event counter and the AF event counter to zero at block 746. The process begins again at block 702 with the classification of the next time period.

After increasing the AF event count at block 706 or increasing the unclassified event count at block 712, if the unclassified event count has not reached the predetermined threshold, "No" of block 713, the combined event count may be compared to a threshold at block 714. When the combined count of the AF event counter and the unclassified event counter has reached a threshold at block 714, e.g., a combined count of three, the AF classification criteria may be adjusted at block 716. In one example, microprocessor 224 adjusts the AF classification criteria by decreasing the AF score threshold to a second lower threshold after classifying a first time period as AF and classifying the next two consecutive time periods as any combination of AF or unclassified based on the first higher AF score threshold as described above. The AF classification criteria may therefore be adjusted in response to three consecutive time periods being classified as AF, a sequence of AF-U-AF or a sequence of AF-U-U.

It is to be understood that in some examples once the combined count reaches a predetermined threshold at block 714, and the AF classification criteria have been adjusted at block 716 prior to an AF detection being made, the AF classification criteria are not adjusted again until AF episode termination is detected, e.g., based on a time period classified as being non-AF (block 708) or based on a predetermined number of unclassified time periods (block 713), e.g., five consecutive unclassified time periods. In other examples, additional adjustments to the AF score may be made before AF episode termination is detected, e.g., to a third AF score threshold or back to the first, highest AF score threshold, as described above.

At block 718, microprocessor 224 compares the AF event count to the AF detection threshold. When the AF detection threshold has not been reached, microprocessor 224 returns to block 702 to obtain the next time period classification. As described above, after adjusting the AF classification criteria at block 716, if a non-AF classification is made ("Yes" branch of block 708) before detecting AF, the AF classification criteria are restored to the initial classification criteria at block 742 and all AF event and unclassified event counters are reset to zero at block 746. If subsequent time periods are classified as AF, "Yes" branch of block 704, the AF event count is increased accordingly at block 706.

If the AF event count reaches a detection threshold, "Yes" branch of block 718, microprocessor 224 detects AF at block 720. An AF detection response is provided at block 721. The response to AF detection may include controlling pace timing and control 212 to deliver an atrial anti-arrhythmia therapy or withhold a ventricular therapy. The response to AF detection may additionally or alternatively include storing data relating to the AF episode, such as the time of onset, the total duration (as determined from the AF event counter upon detection of termination of the AF episode as discussed below or computed using the techniques described in conjunction with FIG. 10), storing an episode of the cardiac electrical signal in RAM 226 and/or other data relating to the AF event. The data may be transmitted to external device 40 (FIG. 1) for displaying or communicating the data to a clinician for use in managing the patient.

When an AF detection is made at block 720, the unclassified event counter is reset to a count of zero at block 722. Microprocessor 224 may begin counting subsequent time periods determined to be unclassified after AF detection is made for detecting termination of the AF episode. The next time period classification is obtained at block 724. If the next time period classification is AF, as determined at block 726, the AF event count is increased at block 728. AF classifications made after AF detection are based on the adjusted AF classification criteria. The AF event counter may continue to be increased with each AF classification made after detecting AF at block 720 for use in determining the duration of the AF episode and determining AF burden (e.g., the combined duration of all detected AF episodes over a given monitoring interval such as 24 hours). Such AF episode data may be transmitted to an external medical device for display or communication to a clinician thereby providing useful information to the clinician in making diagnostic and therapy management decisions.

If the classification of the next time period is not AF, "No" branch of block 726, but is non-AF, "Yes" branch of block 730, termination of the AF episode is detected at block 740. If the classification of the next time period is neither AF nor non-AF, "No" branch of block 730, i.e., if the time period is determined to be unclassified as indicated at block 732, the unclassified event counter is increased by one at block 734. The unclassified event counter is compared to a threshold at block 736. If the threshold is not reached, microprocessor 224 returns to block 724 to fetch the next time period classification. If the unclassified count reaches a threshold at block 736, e.g., five consecutive unclassified time periods, termination of the AF episode is detected at block 740.

If episode termination is detected, the initial AF classification criteria are restored at block 742, and the AF event and unclassified event counters are reset at block 746. The process begins again at block 702.

Figure 12:
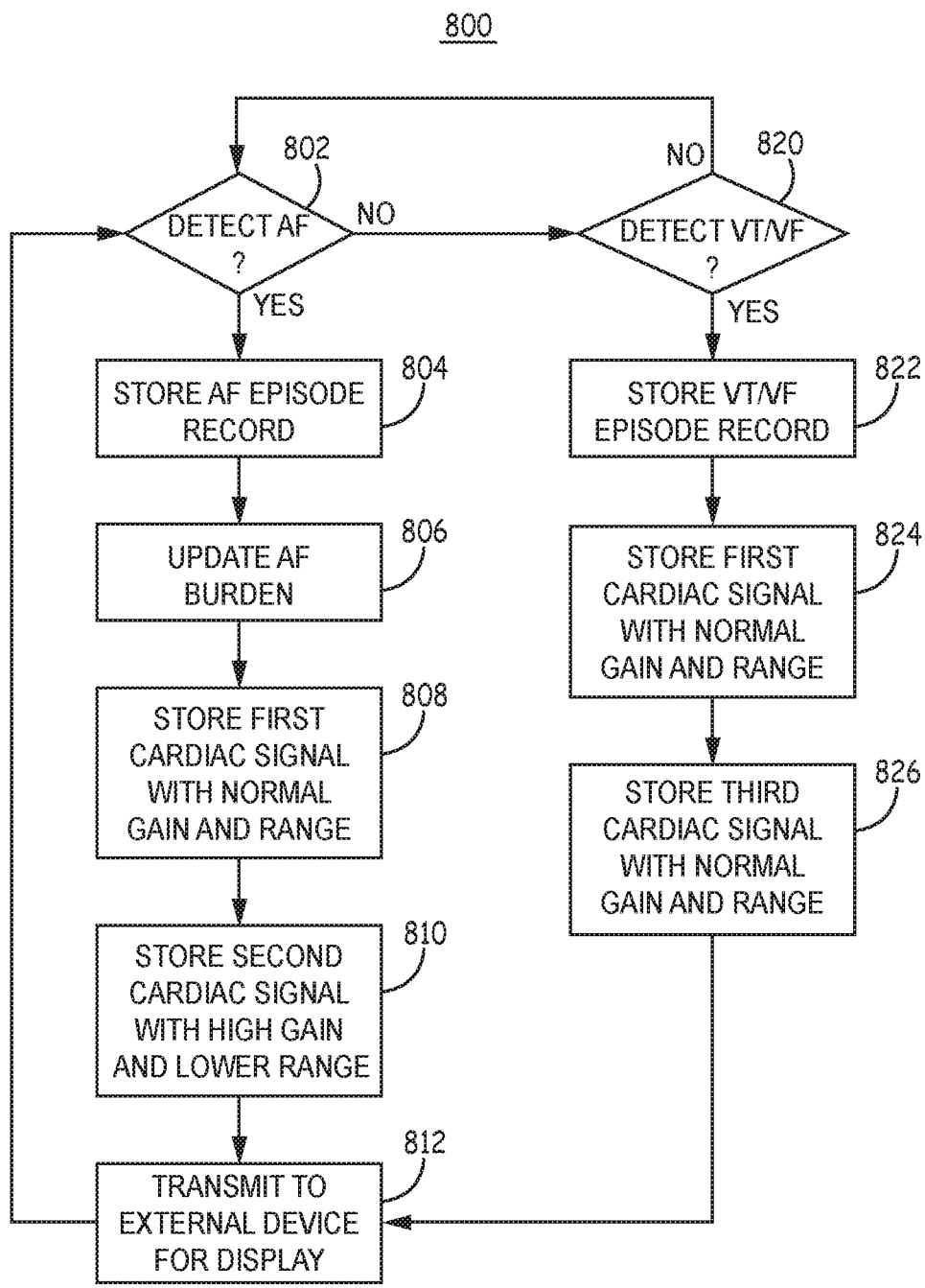
FIG. 12 is a flow chart of a method performed by an ICD or implantable monitor for providing a response to detecting atrial tachyarrhythmia according to one example.

FIG. 12 is a flow chart 800 of a method performed by ICD 10 or ICD 110 for providing a response to detecting AF according to one example. If an AF detection is made at block 802, e.g., as described in conjunction with any of FIGS. 9-11, an AF episode record is stored at block 804. The AF episode record may include a Lorenz plot or histogram of RRI data that led to AF classifications and AF detection. The episode record stored at block 804 may further include the start time, termination time, and total duration of the AF episode. Referring again to FIG. 10, examples of episode durations 615, 635, 655, and 685 are shown extending from the start of the first respective AF classified time period that led to AF detection and ending with the last AF classified time period that leads to detection of termination of the AF episode. Unclassified episodes that lead to termination detection, e.g., unclassified episodes 694 and 696 in scenario (d) may not be included in the episode duration, whereas unclassified episodes that do not immediately precede termination detection, e.g., unclassified episodes 652, 654, 656 and 658 in scenario (c), are included in the episode duration, e.g., duration 655.

When unclassified time periods are included in the AF episode or lead to termination detection of the AF episode, the factor(s) leading to determining the time period as being unclassified may be stored with the AF episode record. For example, if the time period is determined to be unclassified due to other episodes being detected such as VT or VF, due to oversensing, due to too many short RRIs, or due to too many ventricular pacing pulses during the time period, this factor may be stored to provide the clinician with useful information in diagnosing the patient's heart rhythm status for guiding therapy decisions for treating the patient's AF.

At block 806, microprocessor 224 may determine AF burden of the patient by computing the total time AF was identified over a 24-hour time interval (or other predetermined monitoring interval). Computation of the AF burden may include counting or summing all time periods classified as AF or counting or summing only AF classified time periods that were included in a detected AF episode. AF burden may also include all unclassified time periods that occur during a detected AF episode. In some examples, unclassified time periods that lead to detecting termination of the AF episode that are not included in the AF episode duration are not included in the AF burden computation. For example, referring to FIG. 10, scenario (d), unclassified time period 684 is not included in AF burden computation because it occurs before the AF episode indicated by episode duration 685. Unclassified time period 688 is included in AF burden determination because it occurs during the AF episode. Unclassified time periods 694 and 696 are not included in determining AF burden because they lead to termination detection at time 699 and are not included in the episode duration 685.

When AF is detected, microprocessor 224 may store a cardiac signal segment that is acquired during the detected AF episode. The cardiac signal segment is stored in memory at block 808 with the normal gain of sense amplifiers 200 and A/D converter 222 used during cardiac signal analysis and processing performed to identify RRIs, analyze the signal for oversensing, etc. For example, the cardiac signal stored at block 808 may be an EGM signal acquired using RV coil electrode 28 and ICD housing 15 in FIG. 1. In system 100 of FIG. 2A, the cardiac signal stored at block 808 may be an ECG signal acquired using defibrillation electrode 24 or defibrillation electrode 126 and housing 115. The signal stored at normal range (e.g., with 8-bit resolution sampled at 128 Hz with A/D converter input range of ±12 mV) may be used to provide an unclipped EGM or ECG signal for morphology analysis (e.g., wavelet template matching) and for storing unclipped cardiac signal episodes in response to detecting a tachyarrhythmia. The normal range signal stored at block 808 may be selected as a far-field or relatively global cardiac electrical signal that is used to produce a display of the electrical rhythm of the patient's heart clearly showing R-wave morphology and regularity of RRIs for the clinician to see a high level view of the signal and the patient's corresponding rhythm. However, depending on the sensing vector, the normal range cardiac signal stored at block 808 may not include observable or easily observed P-waves.

As such, when AF is detected, the microprocessor 224 stores a second cardiac signal in memory at block 810 with a lower range, higher gain setting, e.g., a range of ±2 mV which may be controlled by adjusting the A/D converter input range. The high gain, lower range setting provides a clearer view of P-waves in the stored cardiac signal segment when displayed by external device 40. The high gain, lower range setting may result in clipping of R-waves in the stored second cardiac signal. However, the first cardiac signal stored at normal range provides a reliable, unclipped display of the R-wave morphology.

The second cardiac signal stored with a high gain, lower range setting may be selected as a second far-field or relatively global signal. For example, in system 1 of FIG. 1, the second cardiac signal may be acquired between the RV coil electrode 24 and the SVC coil electrode 26, or the SVC coil electrode 26 to the ICD housing 15. In the system 100 of FIG. 2A, the second cardiac signal may be acquired using the sensing electrode 128 and sensing electrode 130, one of sensing electrodes 128, 130 or 131 paired with one of defibrillation electrodes 124 or 126, or one of electrodes 124, 126, 128, 130 or 131 paired with housing 115.

When ICD 10 or ICD 110 receives an interrogation command from an external device 40, microprocessor 224 controls telemetry circuit 330 to transmit the AF episode record, AF burden information, and the stored first, normal gain cardiac signal and the second higher gain cardiac signal. The external device is configured to generate a display of the AF data for the patient to provide the clinician with valuable diagnostic information to support therapy decision-making processes.

If AF is not being detected, "No" branch of block 802, microprocessor 224 may be detecting VT or VF at block 820. If not detecting VT or VF, "No" branch of block 820, microprocessor 224 continues monitoring for cardiac tachyarrhythmias at blocks 802 and 820. If AF is not being detected at block 802 but microprocessor 224 is detecting VT or VF, "Yes" branch of block 820, the VT or VF episode record is stored at block 822, which may include rate, duration, start time, end time, delivered therapies and results, etc. At block 824, a segment of the first cardiac signal with normal gain acquired during the detected episode is stored. The first cardiac signal at normal gain may be a far-field or relatively global signal as described above that provides a high level view of R-wave morphology and RRIs and may be the same signal with the same gain that is stored at block 808 in response to AF detection. At block 826, a third cardiac electrical signal is stored with normal gain.

The third cardiac electrical signal may be a near-field or relatively local signal acquired with a different sensing vector than either of the first or second cardiac electrical signals stored at blocks 808 and 810. For example, the third cardiac signal stored at block 826 may be an EGM signal acquired using RV tip electrode 28 and RV ring electrode 30 of system 1 shown in FIG. 1. In system 100 of FIG. 2A, the cardiac signal stored at block 826 may be an ECG signal acquired using sensing electrodes 128 and 130. The third cardiac electrical signal is stored with normal gain but is acquired using a near-field or localized ventricular sensing vector that can be used to generate a display of a high quality ventricular signal when VT or VF is detected and no atrial tachyarrhythmia is detected.

In this way, ICD 10 or ICD 110 provides a unique response for storing data depending on whether an atrial tachyarrhythmia is being detected (with or without concurrent SVT, VT or VF) or a ventricular tachyarrhythmia is being detected (without concurrent AF detection). Storage of a high gain cardiac electrical signal and transmission to an external device 40 for display to a clinician provides the clinician with valuable diagnostic information relating to the detected AF episode. When the AF episode is being detected simultaneously with a ventricular tachyarrhythmia detection, the relationship between events leading to the two detections can be ascertained. However, when only a ventricular tachyarrhythmia is detected, storage and transmission of a near-field or localized ventricular signal may provide the clinician with important information regarding the ventricular rhythm.

In some examples, microprocessor 224 responds to an AF detection by selecting which cardiac electrical signals are stored as described above and transmits the signals with normal gain and range to external device 40. Processor 52 of external device 40 may automatically generate a display on user display 54 that includes the first, high gain, low range signal for observation of P-waves and the second, normal gain, normal range signal for unclipped observation of R-waves.

Figure 13:
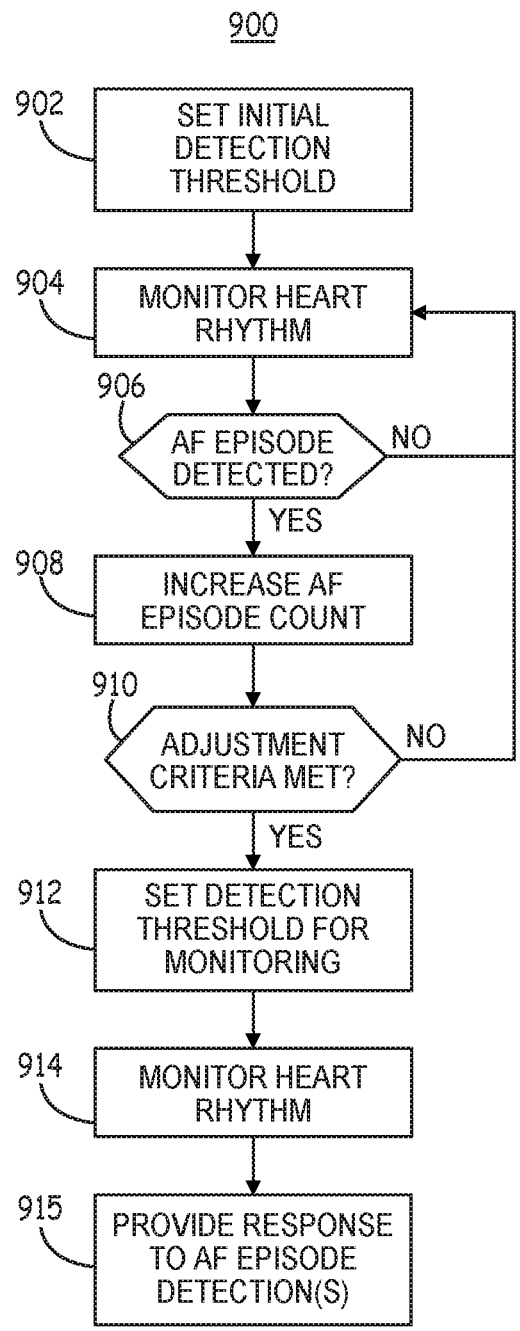
FIG. 13 is a flow chart of a method performed by an implantable medical device system, such as the ICD system of FIG. 1 or the ICD system of FIGS. 2A and 2B, for automatically adjusting a detection threshold required to detect an atrial tachyarrhythmia, such as AF.

FIG. 13 is a flow chart 900 of a method performed by an implantable medical device system, such as a system including ICD 10 and lead 16 or ICD 100 and lead 116, for automatically adjusting a detection threshold required to detect an atrial tachyarrhythmia, such as AF. The detection threshold may be a minimum time duration that the cardiac electrical signal received by sensing circuitry of the ICD must correspond to, or be classified as, the atrial tachyarrhythmia in order to detect the atrial tachyarrhythmia episode. This detection threshold may be defined as a time interval in some atrial tachyarrhythmia detection algorithms. In other examples, the detection threshold may be defined as a threshold number of time predetermined periods required to be classified as AF in order to detect an AF episode, e.g., as generally described in conjunction with FIGS. 9, 10 and 11. In the illustrative examples provided herein, the time periods are two minutes long and the threshold number of time periods that are required to be classified as AF in order to detect an AF episode is three time periods. In other words, a total time duration of at least six minutes of the cardiac electrical signal needs correspond to AF, e.g., be classified as AF based on an AF score and other factors, in order to detect AF. The six minutes are not necessarily consecutive since one or more two-minute time periods that are unclassified may occur between the three time periods classified as AF. In the flow chart of FIG. 13, the microprocessor 224 of ICD 10 or 110 may automatically adjust the detection threshold by adjusting the number of time periods classified as AF that are required in order to detect an AF episode. For example, microprocessor 224 may be configured to automatically adjust the detection threshold by adjusting a count threshold applied to the AF event counter that is used to count the number of time periods that are classified as AF (see blocks 706 and 718 of FIG. 11).

At block 902, microprocessor 224 may set an initial detection threshold. For example, the initial detection threshold may be three two-minute time periods, for a total time duration of six minutes of the cardiac electrical signal being classified as AF. The detection threshold may generally represent the minimum duration of time that the cardiac signal is required to present an AF rhythm and, depending on the particular AF detection algorithm implemented in the ICD 10 or 110, may be expressed as a time interval, e.g., 6 minutes, rather than the value of an AF event counter that counts the number of time periods classified as AF. The initial detection threshold may be set to a relatively low value in order to achieve a relatively high sensitivity for detecting AF episodes. In this way, a patient that is unknown to experience AF, or the characteristics of the AF or AF burden are unknown for a given patient, AF episodes will be detected with relatively high sensitivity initially, e.g., beginning after ICD implantation.

The processor 224 ICD 10 or 110 monitors the heart rhythm at block 904 according to the implemented AF detection algorithm using the initial detection threshold. For example, the heart rhythm may be monitored according to the techniques described above in conjunction with FIGS. 5-11 for detecting an AF episode based on the initial detection threshold of n time periods (e.g., three time periods) being classified as AF. If AF is detected at block 906 based on the initial detection threshold, "yes" branch of block 906, an AF episode counter is increased at block 908.

Microprocessor 224 determines if detection threshold adjustment criteria are met at block 910. This determination may be made by comparing the AF episode counter to an AF monitoring threshold count at block 910. If the count of AF episodes detected based on the initial detection threshold has not reached the AF monitoring threshold count at block 910, the ICD continues monitoring the heart rhythm at block 904 using the initial detection threshold.

In one example, the AF monitoring threshold count applied at block 910 is a count of three AF episodes detected based on the initial detection threshold. If the AF episode count has not reached a value of three detected AF episodes, the heart rhythm continues to be monitored at block 904 using the initial detection threshold. A relatively sensitive AF detection threshold, e.g., a relatively short total time duration or number of time periods classified as AF continues to be used for detecting AF episodes for identifying how likely the patient is to experience AF and how often.

In other examples, the detection threshold adjustment criteria applied to detected AF episodes at block 910 may include a frequency and/or duration of detected AF episodes. For instance, a threshold count may be required to be reached within a predetermined time period. In one example, at least five AF episodes may be required to be detected within 30 days in order for the detection threshold adjustment criteria to be satisfied at block 910. In another example, at least one detected AF episode may be required to have an episode duration that is greater than a predetermined threshold duration, e.g., at least 10 minutes. In yet another example, the detection threshold adjustment criteria applied at block 910 may be based on an AF burden threshold. For example, the criteria at block 910 may require that the summed episode durations of AF episodes detected based on the initial detection threshold within a predetermined time period meets an AF burden threshold. For instance, the summed episode durations of detected AF episodes may be required to reach a cumulative duration of at least 15 minutes within a 24-hour period.

The detection threshold adjustment criteria may include multiple criteria, and when any one of the criterion are met, the detection threshold may be adjusted. In one example, the adjustment criteria may include a first threshold number of detected AF episodes, a second threshold number of episodes detected within a predetermined time interval, a threshold episode duration, and/or a threshold AF burden. If any one of these thresholds is reached, the detection threshold may be adjusted. To illustrate, the detection threshold adjustment criteria may be met if the AF episode counter reaches a total count of 5 detected AF episodes; if the AF episode counter reaches a count of 3 detected AF episodes within 30 days; if a detected AF episode has an episode duration of at least 10 minutes; or if the AF burden has reached at least 15 minutes of cumulative AF episode durations within 24 hours. The number of detected AF episodes, the frequency of detected AF episodes, the maximum episode duration of detected AF episodes, and/or the AF burden may be used alone or in any combination for determining if detection threshold adjustment are met at block 910. The example values of the thresholds given above are intended to be illustrative in nature with no limitation intended. Numerous other examples of combinations of multiple criteria and corresponding threshold values may be conceived based on the examples given herein.

If the detected AF episodes satisfy the detection threshold adjustment criteria at block 910, microprocessor 224 adjusts the detection threshold at block 912. The detection threshold may be adjusted to a value that is greater than or less than the initial detection threshold. In one example, the detection threshold is adjusted to reduce the sensitivity to detecting AF by increasing the minimum time duration or number of AF-classified time periods that are required to detect an AF episode. For instance, if the initial detection threshold is three two-minute time periods, the adjusted detection threshold may be five two-minute time periods required to be classified as AF in order to detect an AF episode. The reduced sensitivity to AF detection may avoid false AF detection and reduce the number of AF episodes for which data is stored in memory of the ICD that requires review or verification by a clinician, easing clinician burden while still capturing important AF episode data.

At block 914, ICD 10 or 110 monitors the heart rhythm for detecting AF according to the implemented AF detection scheme, e.g., as described in conjunction with FIGS. 5 through 11, using the adjusted detection threshold. The longer time duration of the AF detection threshold (e.g., five two-minute time periods instead of three two-minute time periods) may reduce the sensitivity of AF detection but may increase the specificity of AF detection for long-term monitoring of the patient.

In other examples, the AF detection threshold may be adjusted to a lower value at block 912 that increases AF detection sensitivity. In some cases, a clinician may prefer AF detection episodes be detected with greater sensitivity once AF is identified in a given patient based on a less sensitive AF detection threshold. In this case, the AF detection threshold may be reduced to a shorter total time duration, or fewer time periods classified as AF, in order to detect an AF episode.

Microprocessor 224 may execute a response to detecting an AF episode at block 915. The response to an AF episode detection may include one or more of storing AF episode data which may include a segment of the cardiac electrical signal received during the detected AF episode, updating an AF burden, withholding, delaying or adjusting a therapy, and/or withholding delaying or adjusting a ventricular tachyarrhythmia detection.

Figure 14:
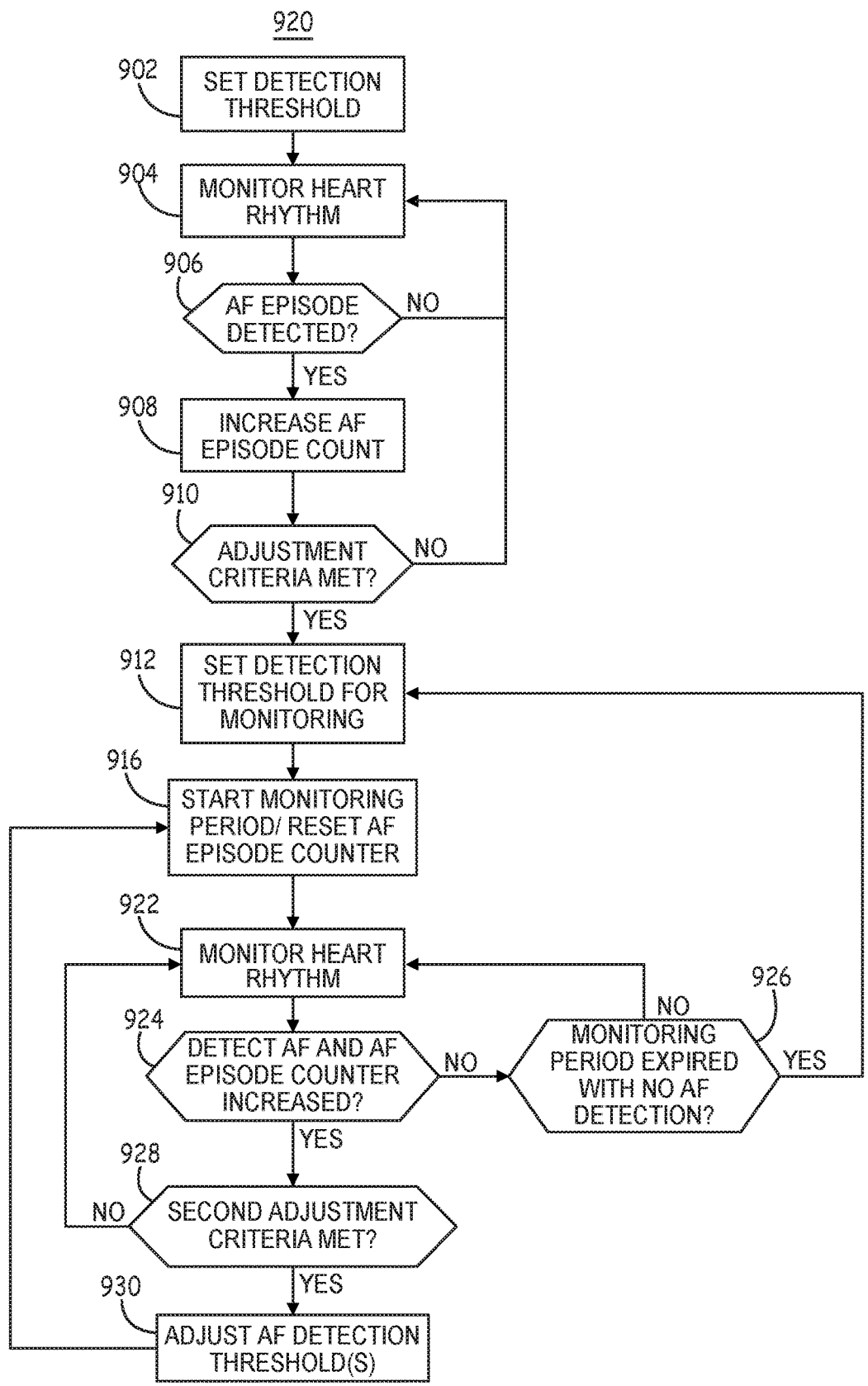
FIG. 14 is a flow chart of a method for automatically adjusting a detection threshold for detecting AF according to another example.

FIG. 14 is a flow chart 920 of a method for automatically adjusting a detection threshold for detecting AF according to another example. Blocks 902 through 912 correspond to identically-numbered blocks of FIG. 13. After adjusting the detection threshold at block 912 in response to one or more AF episodes detected based on the initial detection threshold satisfying the detection threshold adjustment criteria at block 910, a monitoring period is started at block 916. The monitoring period may be a predetermined time period used to control how long the detection threshold remains at the adjusted value. The monitoring period may be a predetermined number of hours, days or weeks. In one example, the monitoring period is 90 days.

At block 922, the heart rhythm is monitored according to the implemented AF detection techniques, e.g., as described above in conjunction with FIGS. 5 through 11. If an AF episode is detected causing the AF episode counter to be increased, "yes" branch of block 924, microprocessor 224 may determine if second detection threshold adjustment criteria are met at block 928. If the second detection threshold adjustment criteria are not satisfied at block 928, the microprocessor returns to block 922 to continue monitoring the heart rhythm using the detection threshold set at block 912.

During the monitoring period, however, the AF detection threshold may be adjusted from the detection threshold set at block 912 when the number and/or frequency of AF episode detections made based on the adjusted detection threshold satisfy second threshold adjustment criteria at block 928. For instance, if the AF episode counter reaches a count of two AF episodes detected using the adjusted AF detection threshold, the AF detection threshold may be adjusted again at block 930. In another example, the second detection threshold adjustment criteria applied at block 928 may require that at least two AF episodes are detected within a predetermined time period that is shorter than the monitoring period, e.g., two AF episode detections within thirty days. If the required frequency of AF episode detections occurs during the monitoring period, the AF detection threshold is adjusted at block 930. The second detection threshold adjustment criteria may require a threshold count of AF episode detections based on the adjusted detection threshold, a threshold frequency of AF episode detections based on the adjusted detection threshold, an AF episode duration equal to or greater than a duration threshold, an AF burden equal to or greater than an AF burden threshold, or any combination thereof.

The AF detection threshold may be adjusted to be less sensitive to increase the specificity of AF detection. For instance, the total time duration required to detect AF may be increased, e.g., from 10 minutes or 5 two-minute time periods classified as AF to 20 minutes or 10 two-minute time periods classified as AF. After adjusting the AF detection threshold at block 930, the microprocessor 224 returns to block 916 to start a new monitoring period. The AF episode counter used to track the number of AF episodes detected during a monitoring period may be reset to zero. The microprocessor 224 continues to monitor the heart rhythm at block 922 using the most recently adjusted AF detection threshold.

In some examples, in addition to or alternatively to adjusting the total time duration or number of time periods classified as AF at block 930, the AF score threshold may be adjusted at block 930. The AF score threshold may be set to first and second values as described in conjunction with FIG. 10 as two-minute time periods are being classified. One or both of the first AF score threshold 602 and the second AF score threshold 604 (shown in FIG. 10) may be adjusted at block 930 for use in classifying a two-minute time period. For example, the AF score threshold may initially be set to a first threshold 602 of 50 for classifying an initial time period as AF and reduced to a second threshold 604 of 38. At block 930, the AF score threshold may be increased to less sensitive settings where the first threshold 602 is set to 60 and the second threshold 604 is set to 45.

If the monitoring period expires ("yes" branch of block 926) before any AF episodes are detected based on the adjusted AF detection threshold ("no" branch of block 924), the microprocessor 224 returns to block 912 and resets the detection threshold (if previously adjusted at block 930) to the previous detection threshold used for chronic monitoring at block 912. For example, if a second adjustment of the AF detection threshold is made at block 930 and a new monitoring period is started at block 916, but the monitoring period expires at block 926 with no AF episodes being detected during the monitoring period, the AF detection threshold is returned to the first adjusted value set at block 912. In the illustrative example given above, an initial detection threshold may be 6 minutes set at block 902, which is adjusted to 10 minutes at block 912, and may be adjusted again to 20 minutes at block 930. If no AF episodes are detected during a monitoring period when the AF detection threshold corresponds to a total time duration of 20 minutes of the cardiac electrical signal being classified as AF, the AF detection threshold may be adjusted back to the 10 minute duration (e.g., 5 two-minute time periods classified as AF).

In some cases, the AF detection threshold is adjusted back to the preceding AF detection threshold value if the monitoring period expires at block 926. Continuing with the illustrative example given above, if the AF detection threshold is currently set at 10 minutes or 5 two-minute time periods classified as AF, the AF detection threshold is adjusted back to 6 minutes or 3 two-minute time periods. In other examples, instead of returning to block 912 when the monitoring period expires with no AF detection, the process may return to block 902 to set the detection threshold to the initial value, e.g., 6 minutes or 3 two-minute time periods in the example given above.

While not explicitly shown in flow chart 920 of FIG. 14, it is to be understood that upon detecting an AF episode at block 906 and/or block 924, microprocessor 224 may control the ICD to provide a response to AF episode detection as described above in conjunction with block 915 of FIG. 13 or any of the AF episode detection responses described in conjunction with block 721 of FIG. 11.

Figure 15:
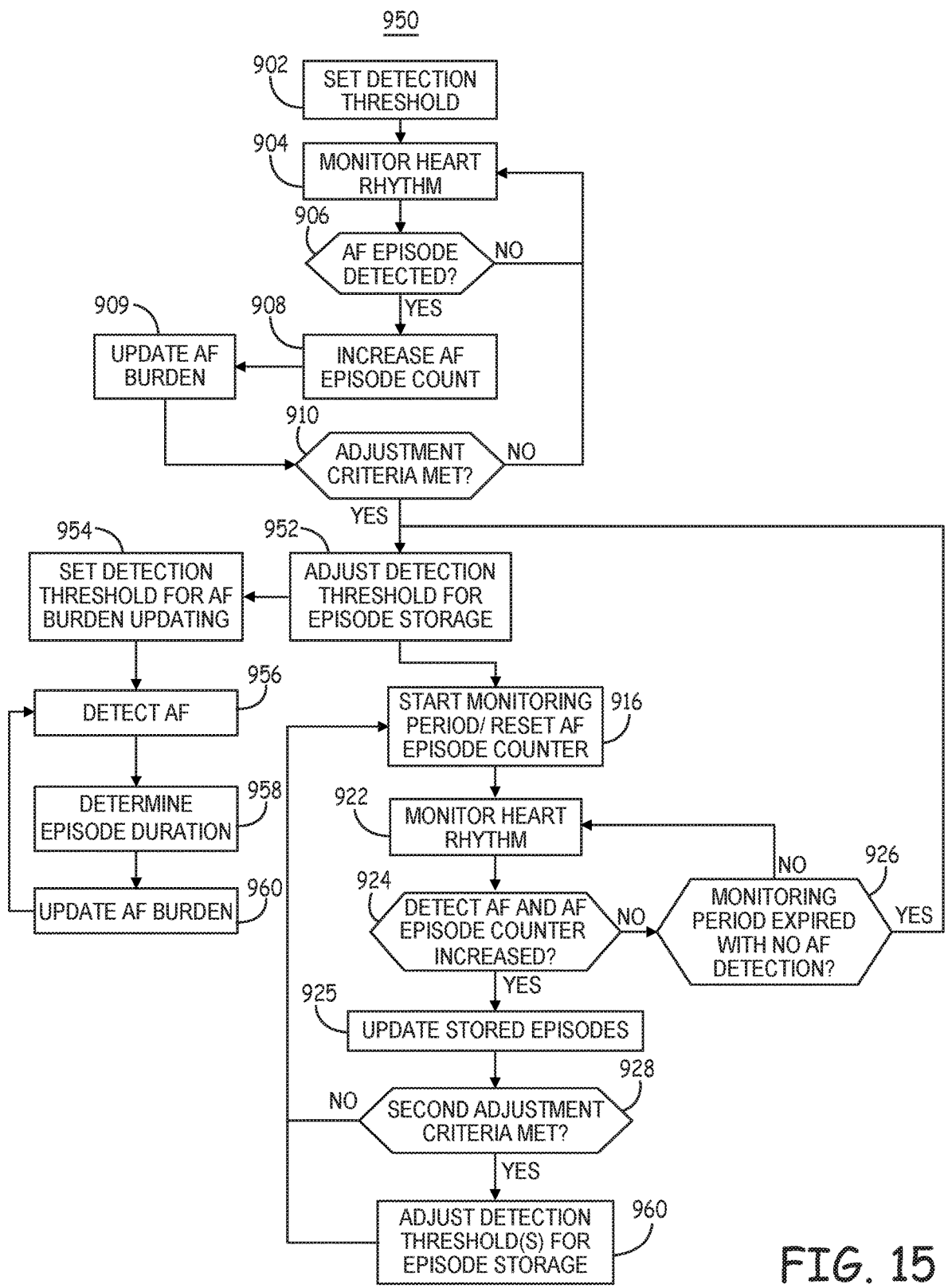
FIG. 15 is a flow chart of a method for detecting AF and determining AF burden according to another example.

FIG. 15 is a flow chart 950 of a method for detecting AF and determining AF burden by a cardiac medical device according to another example. The techniques described above for adjusting the AF detection threshold may be used to control detection of AF episodes for providing a response of storing AF episode data such as a cardiac signal segment, e.g., as described in conjunction with FIG. 12. Other AF episode detection responses, however, may be made by ICD 10 or ICD 110 based on a different AF detection threshold, which may not be automatically adjustable. Other responses to detecting an AF episode that may be made by ICD 10 or ICD 110 may include determining AF burden. AF burden may be determined by summing the AF episode durations for all AF episodes detected over a 24 hour period or other predetermined time period. In some cases, a different AF detection threshold is used for detecting AF episodes for determining AF burden than the AF detection threshold that is used for detecting AF episodes for which a cardiac electrical signal segment is stored.

In flow chart 950, the blocks 902, 904, 906, 908 and 910 correspond to identically numbered blocks described above in conjunction with flow chart 900 of FIG. 13. However, in addition to determining whether detection threshold adjustment criteria are met at block 910 after increasing the AF episode count at block 908, the AF burden may be updated by microprocessor 224 at block 909 by summing the duration of the AF episode detected at block 906 with the episode durations of any AF episodes detected previously within a predetermined AF burden time interval. For example, the AF burden may be determined and stored for each consecutive 24 hour time interval or for a running 24 hour time interval. In other examples, the AF burden may be determined over another moving predetermined time interval.

If the detection threshold adjustment criteria are met at block 910, as described above in conjunction with FIG. 13, the detection threshold for AF episode storage is adjusted at block 952. The adjustment to the detection threshold at block 952 may be an increase in the total time duration, e.g., defined as the number of two-minute time periods classified as AF as described above in conjunction with FIGS. 13-14. For example, the detection threshold used for triggering AF episode storage may be adjusted from 6 minutes (or 3 two-minute time periods) to 10 minutes (or 5 two-minute time periods) of the cardiac electrical signal being classified as AF.

The detection threshold used for updating the AF burden, however, may be kept the same as the initial detection threshold set at block 902 or adjusted to a detection threshold different than the detection threshold set at block 952 for AF episode storage. The detection threshold for updating the AF burden is set at block 954. In some cases, the detection threshold for updating AF burden is set or maintained at a more sensitive setting than the detection threshold set at block 952 for episode storage. For example, the detection threshold for updating AF burden may be kept at 6 minutes or a count of 3 two-minute time periods classified as AF, and the detection threshold set at block 952 for episode storage is set to a relatively less sensitive setting of 10 minutes or a count of 5 two-minute time periods classified as AF. In this way, the AF burden is determined with relatively high sensitivity and relatively low specificity while AF episodes that may be stored for review by a clinician are detected with relatively higher specificity and relatively lower sensitivity than the AF episodes detected for updating the AF burden.

When an AF episode is detected at block 956 based on the detection threshold set at block 954 (or kept the same as the initial detection threshold), the duration of the detected episode is determined at block 958. The duration of the detected episode may be determined using the methods described above in conjunction with FIGS. 9 and 10. Microprocessor 224 updates the AF burden at block 960 using the determined episode duration. The episode duration may be summed with the duration(s) of previous AF episode(s) that have been detected since the start of the AF burden time period, e.g., since the start of a 24-hour time period.

The process of updating the AF burden at block 960 continues by returning to block 956 to wait for the next AF episode detected based on the detection threshold set at block 954. The detection threshold used for detecting AF episodes used to update the AF burden may not be automatically adjusted by microprocessor 224 in some examples and may remain fixed at the initial detection threshold set at block 902 or set to a user-programmed value. In other examples, the detection threshold used for updating AF burden may be adjusted once at block 954 from the initial detection threshold set at block 902 after the detection threshold adjustment criteria are met at block 910 and not adjusted again. In still other examples, the detection threshold used for updating the AF burden, storing AF episode data such as a cardiac electrical signal segment and/or providing other responses to AF detection by ICD may be adjusted to desired values based on adjustment criteria being met in the manner described above in conjunction with FIGS. 13 and 14.

In the example of FIG. 15, however, the detection threshold is adjusted at block 952 to a relatively less sensitive setting than the AF detection threshold set at block 954 for updating AF burden. The adjusted detection threshold value set at block 652 is used for detecting AF episodes for which a cardiac signal segment is to be stored in RAM 226 (or other computer-readable storage media such as the examples given previously herein). Blocks 916, 922, 924, 926 and 928 of flow chart 950 may correspond to identically-numbered blocks described above in conjunction with FIG. 14. In the process of flow chart 950, microprocessor 224 may be configured to provide a response to an AF episode detected at block 924 by updating stored AF episode data at block 925. Methods for updating AF episode data stored in RAM 224 of ICD 10 or 110 are described below in conjunction with FIG. 16.

At block 960, the detection threshold may be adjusted when second AF detection threshold adjustment criteria are met at block 928. The adjustment performed at block 960 may correspond to the adjustment described in conjunction with block 930 of FIG. 14, e.g., to a less sensitive setting for detecting AF, but in the example of FIG. 15, the detection threshold that is adjusted at block 960 is applied only for detecting AF episodes that trigger AF episode data storage at block 925 and is not used for detecting AF episodes that trigger other AF detection responses, such as causing the AF burden to be updated.

Figure 16:
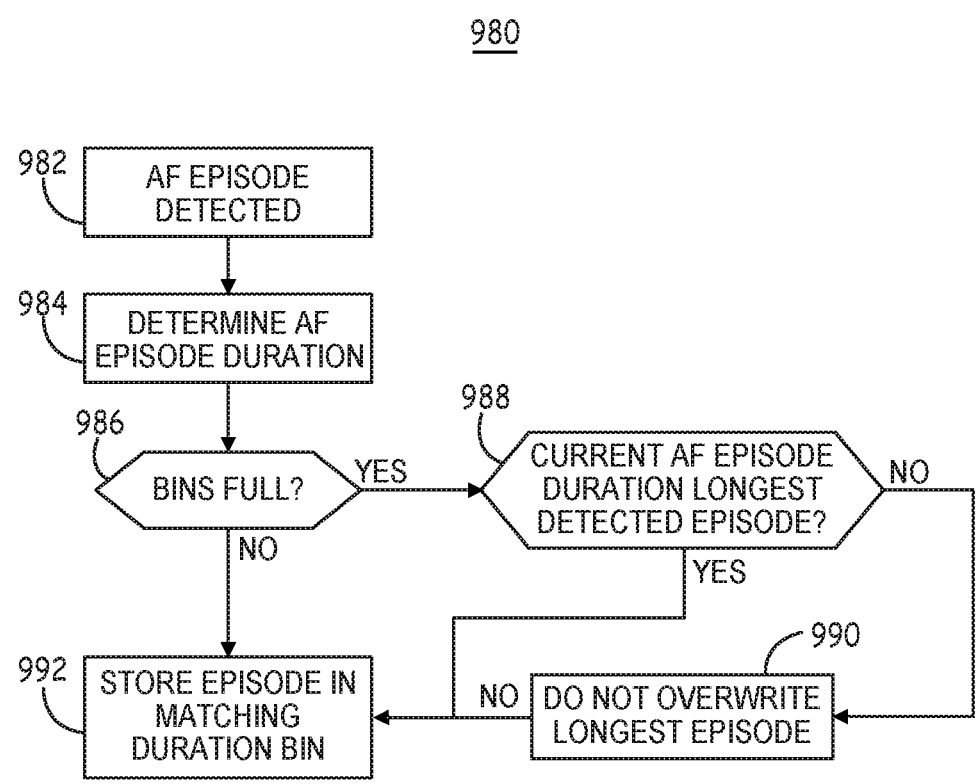
FIG. 16 is a flow chart of a method for storing AF episode data in the memory of an ICD according to one example.

FIG. 16 is a flow chart 980 of a method for responding to AF episode detection by storing AF episode data according to one example. At block 982, an AF episode is detected. The detection of the AF episode at block 982 may be based on an initial AF detection threshold, e.g., a detection made at block 906 based on the initial detection threshold set at block 902 of any of FIG. 13, 14 or 15. In other instances, the detection of the AF episode at block 982 may be an AF detection made based on an adjusted AF detection threshold during heart rhythm monitoring at block 914 of FIG. 13. The process of flow chart 980 for updating detected AF episode storage may be performed at block 915 of FIG. 13.

In other examples, the detection of the AF episode at block 982 is an AF detection made at block 924 in response to an adjusted AF detection threshold as described above in conjunction with FIGS. 14 and 15. In other words, the process for updating AF episodes stored in the memory of the ICD 10 or 110 according to the flow chart 980 may be performed any time AF is detected based on an initial AF detection threshold and/or based on an AF detection threshold that has been adjusted for AF monitoring and AF episode storage. It is to be understood that an AF episode detected at block 956 based on an AF detection threshold set specifically for updating AF burden as described in conjunction with FIG. 15, may be ignored at block 982 of FIG. 16 when a different AF detection threshold has been set for triggering AF episode data storage.

At block 984, the duration of the AF episode detected at block 982 is determined. For example, the AF episode duration may be determined at block 984 using any of the methods described above in conjunction with FIG. 10. At block 986, microprocessor 224 determines if memory bins allocated for AF episode storage are full. If not, a cardiac signal segment acquired during the detected AF episode is stored in ICD memory, e.g., RAM 226, at block 992. In some examples, a predetermined number of bins may be allocated for multiple AF episode durations or episode duration ranges. Each episode duration or duration range may have multiple bins allocated for storing episodes of that specific duration or duration range. For example, three bins may be allocated for storing AF episodes having an episode duration that is equal to or greater than an initial detection threshold but less than an adjusted detection threshold and three bins may be allocated for storing AF episodes having a duration that is equal to or greater than the adjusted detection threshold.

In the examples given above, three bins may be allocated for storing cardiac electrical signal segments acquired during AF episodes having an episode duration that is at least the initial detection threshold of 6 minutes or 3 two-minute time periods but less than the adjusted detection threshold of 10 minutes or 5 two-minute time periods. Three other bins may be allocated for storing cardiac electrical signal segments that are acquired during an AF episode having an episode duration that is at least the adjusted detection threshold of 10 minutes or 5 two-minute time periods. In this way, a cardiac electrical signal segment may be stored for each of up to three AF episodes detected using the 6 minute detection threshold and having an episode duration that is less than 10 minutes and cardiac electrical signal segments may be stored for each of up to three AF episodes having an episode duration that is equal to or greater than 10 minutes, regardless of the detection threshold used to detect the AF episode.

In other examples, memory bins may be allocated according to the detection threshold used to detect the AF episode. For example, three bins may be allocated for storing a cardiac electrical signal segment acquired during an AF episode detected based on the initial detection threshold, and three bins may be allocated for storing a cardiac electrical signal segment acquired during an AF episode detected based on an adjusted detection threshold. Additional bins may be allocated for each detection threshold used when two or more adjustments to the detection threshold are made.

The episode duration determined at block 984 may be used to determine which bin the cardiac electrical signal segment is written to at block 992. The cardiac electrical signal segment is written to a bin allocated to an episode duration or range matching or including the determined episode duration. In other examples, the detection threshold used to detect the AF episode is used to determine which bin the cardiac electrical signal segment is written to at block 992. The cardiac electrical signal segment is written to a bin allocated to the detection threshold used to detect the AF episode.

If the bins allocated to the corresponding AF episode duration or detection threshold are not full, "no" branch of block 986, the cardiac electrical signal segment is written to any of the unoccupied bins allocated for that AF episode duration or detection threshold. If the bins allocated for the corresponding episode duration or detection threshold are full, "yes" branch of block 986, microprocessor 224 determines at block 988 if the currently detected AF episode has an episode duration that is longer than any currently stored AF episodes. If a cardiac electrical signal segment is stored for an AF episode having a longer episode duration than the most recently detected AF episode, the data stored for the longest duration AF episode is not overwritten as indicated at block 990. Another occupied bin allocated to the corresponding duration or detection threshold of the most recently detected AF episode is overwritten at block 992 to store the cardiac electrical signal segment corresponding to the most recently detected AF episode. The bin that is overwritten may be the bin storing the oldest AF episode data such that the cardiac electrical signal segments (and any other AF episode data) are stored in a first-in-first-out basis with the exception of retaining AF episode cardiac signal segment stored for the longest duration AF episode, regardless of age by not overwriting the data stored for the longest duration AF episode when a newer AF episode is detected. In this way, data for both the most recently occurring AF episodes and data for the AF episode having the longest episode duration, regardless of how long ago the longest episode was detected, are accumulated in ICD memory.

If the most recently detected AF episode has a longer episode duration than any of the stored episodes, "yes" branch of block 988, a cardiac electrical signal segment is stored at block 992 by overwriting the oldest data in a bin allocated for the corresponding episode duration or detection threshold. It is recognized that when ICD 10 or 110 is interrogated by an external device, e.g., external device 40 (shown in FIG. 1), data stored in all bins may be transmitted to the external device and all bins allocated for storing AF episode data may be cleared.

When the method of FIG. 16 is used to control storing of cardiac signal segments in response to AF episode detection, the AF episodes detected using the adjusted AF detection threshold that has been increased to achieve relatively higher specificity and relatively lower sensitivity promotes storage of true AF episodes. The likelihood of storing data corresponding to false AF episodes is reduced, thereby reducing the burden placed on a clinician in reviewing AF episode data that does not correspond to true AF episodes.

While the examples disclosed herein refer primarily to the detection of AF, it is contemplated that aspects of the techniques of the present disclosure may be utilized for detecting and responding to other atrial tachyarrhythmia episodes, such as atrial flutter and atrial tachycardia.

Thus, an apparatus and methods have been presented in the foregoing description for detecting and responding to atrial tachyarrhythmia with reference to specific examples. It is appreciated that various modifications to the referenced examples may be made, including modifying the order of steps performed and/or modifying the combinations of operations shown in the flow charts presented herein, without departing from the scope of the following claims.

The invention claimed is:

1. A device comprising:
sensing circuitry configured to receive a cardiac electrical signal; and
a processor configured to:
 detect a plurality of first atrial tachyarrhythmia episodes within the cardiac electrical signal, each of the plurality of first atrial tachyarrhythmia episodes detected in response to the cardiac electrical signal being classified as an atrial tachyarrhythmia for a time duration greater than a first detection threshold time period;
 determine that detection adjustment criteria are met;
 adjust the device to operate in accordance with a second detection threshold time period in response to the detection adjustment criteria being met, the second detection threshold time period being longer than the first detection threshold time period; and
 detect at least one second atrial tachyarrhythmia episode within the cardiac electrical signal in response to the cardiac electrical signal being classified as an atrial tachyarrhythmia for a time duration greater than the second detection threshold time period.

2. The device of claim 1, wherein the processor is configured to:
increase an atrial tachyarrhythmia counter in response to detecting each of the plurality of the first atrial tachyarrhythmia episodes;
determine that the atrial tachyarrhythmia counter exceeds a threshold count; and
determine that detection adjustment criteria are met based at least on the determination that the atrial tachyarrhythmia counter exceeds the threshold count.

3. The device of claim 2, wherein processor is configured to:
determine episode durations for each of the plurality of first atrial tachyarrhythmia episodes;
determine that at least one of the episode durations is greater than a predetermined duration threshold; and
determine that the detection threshold adjustment criteria are met based at least on the determination that the atrial tachyarrhythmia counter exceeds the threshold count and the determination that at least one of the episode durations is greater than the predetermined duration threshold.

4. The device of claim 2, wherein the processor is configured to:
determine an amount of time that has elapsed since detecting the first of the plurality of first atrial tachyarrhythmia episodes;
determine that the amount of time that has elapsed since detecting the first of the plurality of first atrial tachyarrhythmia episodes is less than a predetermined time period; and
determine that the detection threshold adjustment criteria are met based at least on the determination that the atrial tachyarrhythmia counter exceeds the threshold count and the determination that the amount of time that has elapsed since detecting the first of the plurality of first atrial tachyarrhythmia episodes is less than the predetermined time period.

5. The device of claim 1, wherein processor is configured to:
determine episode durations for each of the plurality of first atrial tachyarrhythmia episodes;
determine that at least one of the episode durations is greater than a predetermined duration threshold; and
determine that the detection threshold adjustment criteria are met based at least on the determination that at least one of the episode durations is greater than the predetermined duration threshold.

6. The device of claim 1, wherein the processor is configured to:
compute an atrial tachyarrhythmia burden based on at least a portion of the plurality of first atrial tachyarrhythmia episodes;
determining that the computed atrial tachyarrhythmia burden is greater than an atrial tachyarrhythmia burden threshold; and
determine that the detection threshold adjustment criteria are met based at least on the determination that the computed atrial tachyarrhythmia burden is greater than the atrial tachyarrhythmia burden threshold.

7. The device of claim 6, wherein the processor is configured to compute the atrial tachyarrhythmia burden by computing a combined duration of the plurality of first atrial tachyarrhythmia episodes over a predetermined timed interval.

8. The device of claim 1, wherein the processor is further configured to determine that the detection threshold adjustment criteria are met in response to at least one of:
any of the plurality of first atrial tachyarrhythmia episodes having an episode duration that is greater than a predetermined duration threshold;
the number of the plurality of first atrial tachyarrhythmia episodes exceeding a first predetermined threshold number;
the number of the plurality of first atrial tachyarrhythmia episodes exceeding a second predetermined threshold number within a predetermined time period; or
an atrial tachyarrhythmia burden of the plurality of first atrial tachyarrhythmia episodes exceeding an atrial tachyarrhythmia burden threshold.

9. The device of claim 1, wherein the processor is further configured to:
adjust the second detection threshold time period back to the first detection threshold time period in response to a predetermined amount of time expiring without detecting at least one second atrial tachyarrhythmia episode within the cardiac based on the second detection threshold time period.

10. The device of claim 1, wherein the processor is further configured to provide a response to the detection of one or more of the plurality of first atrial tachyarrhythmia episodes or the second atrial tachyarrhythmia episode, the response comprising at least one of:
controlling therapy circuitry within the system to withhold a therapy, adjust the therapy, or deliver the therapy;
controlling a patient notification system to generate a patient alert;
transmitting data via telemetry circuit to alert a clinician or a patient; and/or
triggering a second signal acquisition or analysis.

11. A method comprising:
obtaining a cardiac electrical signal; and
detecting a plurality of first atrial tachyarrhythmia episodes within the cardiac electrical signal, each of the plurality of first atrial tachyarrhythmia episodes detected in response to the cardiac electrical signal being classified as an atrial tachyarrhythmia for a time duration greater than a first detection threshold time period;
determining that detection adjustment criteria are met;
adjusting the device to operate in accordance with a second detection threshold time period in response to the detection adjustment criteria being met, the second detection threshold time period being longer than the first detection threshold time period; and
detecting at least one second atrial tachyarrhythmia episode within the cardiac electrical signal in response to the cardiac electrical signal being classified as an atrial tachyarrhythmia for a time duration greater than the second detection threshold time period.

12. The method of claim 11, further comprising:
increasing an atrial tachyarrhythmia counter in response to detecting each of the plurality of the first atrial tachyarrhythmia episodes; and
determining that the atrial tachyarrhythmia counter exceeds a threshold count;
wherein determining that detection adjustment criteria are met comprises determining that the detection adjustment criteria are met based the determining that at least on the atrial tachyarrhythmia counter exceeding the threshold count.

13. The method of claim 12, further comprising:
determining episode durations for each of the plurality of first atrial tachyarrhythmia episodes; and
determining that at least one of the episode durations is greater than a predetermined duration threshold;
wherein determining that detection adjustment criteria are met comprises determining that the detection adjustment criteria are met based at least on the determining that the atrial tachyarrhythmia counter exceeds the threshold count and the determining that at least one of the episode durations is greater than the predetermined duration threshold.

14. The method of claim 12, further comprising:
determining an amount of time that has elapsed since detecting the first of the plurality of first atrial tachyarrhythmia episodes; and
determining that the amount of time that has elapsed since detecting the first of the plurality of first atrial tachyarrhythmia episodes is less than a predetermined time period;
wherein determining that detection adjustment criteria are met comprises determining that the detection adjustment criteria are met based at least on the determining that the atrial tachyarrhythmia counter exceeds the threshold count and the determining that the amount of time that has elapsed since detecting the first of the plurality of first atrial tachyarrhythmia episodes is less than the predetermined time period.

15. The method of claim 11, further comprising:
determining episode durations for each of the plurality of first atrial tachyarrhythmia episodes; and
determining that at least one of the episode durations is greater than a predetermined duration threshold;
wherein determining that detection adjustment criteria are met comprises determining that the detection adjustment criteria are met based at least on the determining that at least one of the episode durations is greater than the predetermined duration threshold.

16. The method of claim 11, further comprising:
computing an atrial tachyarrhythmia burden based on at least a portion of the plurality of first atrial tachyarrhythmia episodes; and
determining that the computed atrial tachyarrhythmia burden is greater than an atrial tachyarrhythmia burden threshold;
wherein determining that detection adjustment criteria are met comprises determining that the detection adjustment criteria are met based at least on the determining that the computed atrial tachyarrhythmia burden is greater than the atrial tachyarrhythmia burden threshold.

17. The method of claim 16, wherein computing the atrial tachyarrhythmia burden comprises summing a duration of the plurality of first atrial tachyarrhythmia episodes over a predetermined timed interval.

18. The method of claim 11, wherein determining that detection adjustment criteria are met comprises determining that the detection adjustment criteria are met in response to at least one of:
determining that any of the plurality of first atrial tachyarrhythmia episodes have an episode duration that is greater than a predetermined duration threshold;
determining that the number of the plurality of first atrial tachyarrhythmia episodes exceeds a first predetermined threshold number;
determining that the number of the plurality of first atrial tachyarrhythmia episodes exceeds a second predetermined threshold number within a predetermined time period; or
determining that an atrial tachyarrhythmia burden of the plurality of first atrial tachyarrhythmia episodes exceeds an atrial tachyarrhythmia burden threshold.

19. The method of claim 1, further comprising providing a response to the detection of one or more of the plurality of first atrial tachyarrhythmia episodes or the second atrial tachyarrhythmia episode, the response comprising at least one of:
controlling therapy circuitry within the system to withhold a therapy, adjust the therapy, or deliver the therapy;
controlling a patient notification system to generate a patient alert;
transmitting data via telemetry circuit to alert a clinician or a patient; and/or
triggering a second signal acquisition or analysis.

20. A device comprising:
a memory;
a processor coupled to the memory, wherein the processor is configured to allocate a plurality of memory bins of the memory to each one of a plurality of episode duration ranges;

detect an atrial tachyarrhythmia episode;

determine an episode duration of the atrial tachyarrhythmia episode;

determine that that plurality of memory bins allocated to the episode duration range associated with the episode duration are full;

determine that the episode duration of the detected atrial tachyarrhythmia episode is greater than a duration of at least one previously stored atrial tachyarrhythmia episode; and overwriting the memory bin associated with one of the previously stored atrial tachyarrhythmia episodes having the duration that is less than the duration of the detected atrial tachyarrhythmia episode.

* * * * *